(12) United States Patent
Adams et al.

(10) Patent No.: US 12,343,071 B2
(45) Date of Patent: Jul. 1, 2025

(54) VOLTAGE CONTROLLED PULSE SEQUENCES FOR IRREVERSIBLE ELECTROPORATION ABLATIONS

(71) Applicant: Boston Scientific Scimed Inc, Maple Grove, MN (US)

(72) Inventors: Nathaniel Adams, New Richmond, WI (US); Jonathan Tyler Gorzycki, Blaine, MN (US); Randall Dodson, New Hope, MN (US); Brendan Early Koop, Ham Lake, MN (US)

(73) Assignee: Boston Scientific Scimed, Inc, Maple Grove, MN (US)

( * ) Notice: Subject to any disclaimer, the term of this patent is extended or adjusted under 35 U.S.C. 154(b) by 795 days.

(21) Appl. No.: 17/582,733

(22) Filed: Jan. 24, 2022

(65) Prior Publication Data

US 2022/0233237 A1 Jul. 28, 2022

Related U.S. Application Data

(60) Provisional application No. 63/142,133, filed on Jan. 27, 2021.

(51) Int. Cl.
*A61B 18/00* (2006.01)
*A61B 18/12* (2006.01)
*A61B 18/14* (2006.01)

(52) U.S. Cl.
CPC ...... *A61B 18/1492* (2013.01); *A61B 18/1206* (2013.01); *A61B 2018/00577* (2013.01);
(Continued)

(58) Field of Classification Search
None
See application file for complete search history.

(56) References Cited

U.S. PATENT DOCUMENTS 4,200,104 A 4/1980 Harris
4,470,407 A 9/1984 Hussein
(Continued)

FOREIGN PATENT DOCUMENTS

AU 741167 B2 11/2001
EP 1042990 A1 10/2000
(Continued)

OTHER PUBLICATIONS

Du Pre, B.C. et al., "Minimal coronary artery damage by myocardial electroporation ablation," Europace, 15(1):144-149 (2013).
(Continued)

*Primary Examiner* — Linda C Dvorak
*Assistant Examiner* — Nicholas S Borsch
(74) *Attorney, Agent, or Firm* — Nelson Mullins Riley & Scarborough LLP

(57) ABSTRACT

At least some embodiments of the present disclosure are directed to an electroporation ablation system for treating targeted tissue in a patient. The electroporation ablation system comprises an ablation catheter including catheter electrodes configured to generate electric fields in the targeted tissue in response to a plurality of electrical pulse sequences delivered in a plurality of therapy sections; a controller configured to receive a first pulse voltage of a first electrical pulse sequence measured during a first therapy section of the plurality of therapy sections; and determine a charge voltage based on the first pulse voltage; and an electroporation generator. The electroporation generator is operatively coupled to the catheter electrodes and the controller and configured to deliver a second electrical pulse sequence at a controlled pulse voltage for a second therapy section of the plurality of therapy sections.

18 Claims, 8 Drawing Sheets

(52) U.S. Cl.
CPC .............. *A61B 2018/00613* (2013.01); *A61B 2018/00767* (2013.01); *A61B 2018/00827* (2013.01); *A61B 2018/00875* (2013.01); *A61B 2018/00892* (2013.01)

(56) References Cited

U.S. PATENT DOCUMENTS

| | | |
|---|---|---|
| 4,739,759 A | 4/1988 | Rexroth et al. |
| 5,234,004 A | 8/1993 | Hascoet et al. |
| 5,242,441 A | 9/1993 | Avitall |
| 5,257,635 A | 11/1993 | Langberg |
| 5,281,213 A | 1/1994 | Milder et al. |
| 5,304,214 A | 4/1994 | Deford et al. |
| 5,306,296 A | 4/1994 | Wright et al. |
| 5,334,183 A | 8/1994 | Wuchinich |
| 5,334,193 A | 8/1994 | Nardella |
| 5,341,807 A | 8/1994 | Nardella |
| 5,342,301 A | 8/1994 | Saab |
| 5,398,683 A | 3/1995 | Edwards et al. |
| 5,443,463 A | 8/1995 | Stern et al. |
| 5,454,370 A | 10/1995 | Avitall |
| 5,515,848 A | 5/1996 | Corbett et al. |
| 5,531,685 A | 7/1996 | Hemmer et al. |
| 5,545,161 A | 8/1996 | Imran |
| 5,578,040 A | 11/1996 | Smith |
| 5,617,854 A | 4/1997 | Munsif |
| 5,624,430 A | 4/1997 | Eton et al. |
| 5,667,491 A | 9/1997 | Pliquett et al. |
| 5,672,170 A | 9/1997 | Cho et al. |
| 5,700,243 A | 12/1997 | Narciso, Jr. |
| 5,702,438 A | 12/1997 | Avitall |
| 5,706,823 A | 1/1998 | Wodlinger |
| 5,722,400 A | 3/1998 | Ockuly et al. |
| 5,722,402 A | 3/1998 | Swanson et al. |
| 5,749,914 A | 5/1998 | Janssen |
| 5,779,699 A | 7/1998 | Lipson |
| 5,788,692 A | 8/1998 | Campbell et al. |
| 5,810,762 A | 9/1998 | Hofmann |
| 5,833,710 A | 11/1998 | Jacobson |
| 5,836,874 A | 11/1998 | Swanson et al. |
| 5,836,942 A | 11/1998 | Netherly et al. |
| 5,836,947 A | 11/1998 | Fleischman et al. |
| 5,843,154 A | 12/1998 | Osypka |
| 5,849,028 A | 12/1998 | Chen |
| 5,860,974 A | 1/1999 | Abele |
| 5,863,291 A | 1/1999 | Schaer |
| 5,868,736 A | 2/1999 | Swanson et al. |
| 5,871,523 A | 2/1999 | Fleischman et al. |
| 5,876,336 A | 3/1999 | Swanson et al. |
| 5,885,278 A | 3/1999 | Fleischman |
| 5,895,404 A | 4/1999 | Ruiz |
| 5,899,917 A | 5/1999 | Edwards et al. |
| 5,904,709 A | 5/1999 | Arndt et al. |
| 5,916,158 A | 6/1999 | Webster, Jr. |
| 5,916,213 A | 6/1999 | Haissaguerre et al. |
| 5,921,924 A | 7/1999 | Avitall |
| 5,928,269 A | 7/1999 | Alt |
| 5,928,270 A | 7/1999 | Ramsey, III |
| 5,938,660 A | 8/1999 | Swartz et al. |
| 6,002,955 A | 12/1999 | Willems et al. |
| 6,006,131 A | 12/1999 | Cooper et al. |
| 6,009,351 A | 12/1999 | Flachman |
| 6,014,579 A | 1/2000 | Pomeranz et al. |
| 6,029,671 A | 2/2000 | Stevens et al. |
| 6,033,403 A | 3/2000 | Tu et al. |
| 6,035,238 A | 3/2000 | Ingle et al. |
| 6,045,550 A | 4/2000 | Simpson et al. |
| 6,068,653 A | 5/2000 | LaFontaine |
| 6,071,274 A | 6/2000 | Thompson et al. |
| 6,071,281 A | 6/2000 | Burnside et al. |
| 6,074,389 A | 6/2000 | Levine et al. |
| 6,076,012 A | 6/2000 | Swanson et al. |
| 6,090,104 A | 7/2000 | Webster, Jr. |
| 6,096,036 A | 8/2000 | Bowe et al. |
| 6,113,595 A | 9/2000 | Muntermann |
| 6,119,041 A | 9/2000 | Pomeranz et al. |
| 6,120,500 A | 9/2000 | Bednarek et al. |
| 6,142,993 A | 11/2000 | Whayne et al. |
| 6,146,381 A | 11/2000 | Bowe et al. |
| 6,164,283 A | 12/2000 | Lesh |
| 6,167,291 A | 12/2000 | Barajas et al. |
| 6,171,305 B1 | 1/2001 | Sherman |
| 6,216,034 B1 | 4/2001 | Hofmann et al. |
| 6,219,582 B1 | 4/2001 | Hofstad et al. |
| 6,223,085 B1 | 4/2001 | Dann et al. |
| 6,231,518 B1 | 5/2001 | Grabek et al. |
| 6,245,064 B1 | 6/2001 | Lesh et al. |
| 6,251,107 B1 | 6/2001 | Schaer |
| 6,251,109 B1 | 6/2001 | Hassett et al. |
| 6,251,128 B1 | 6/2001 | Knopp et al. |
| 6,270,476 B1 | 8/2001 | Santoianni et al. |
| 6,272,384 B1 | 8/2001 | Simon et al. |
| 6,287,306 B1 | 9/2001 | Kroll et al. |
| 6,314,963 B1 | 11/2001 | Vaska et al. |
| 6,322,559 B1 | 11/2001 | Daulton et al. |
| 6,350,263 B1 | 2/2002 | Wetzig et al. |
| 6,370,412 B1 | 4/2002 | Armoundas et al. |
| 6,391,024 B1 | 5/2002 | Sun et al. |
| 6,447,505 B2 | 9/2002 | McGovern et al. |
| 6,464,699 B1 | 10/2002 | Swanson |
| 6,470,211 B1 | 10/2002 | Ideker et al. |
| 6,502,576 B1 | 1/2003 | Lesh |
| 6,503,247 B2 | 1/2003 | Swartz et al. |
| 6,517,534 B1 | 2/2003 | McGovern et al. |
| 6,527,724 B1 | 3/2003 | Fenici |
| 6,527,767 B2 | 3/2003 | Wang et al. |
| 6,592,581 B2 | 7/2003 | Bowe |
| 6,595,991 B2 | 7/2003 | Toellner et al. |
| 6,607,520 B2 | 8/2003 | Keane |
| 6,613,046 B1 | 9/2003 | Jenkins et al. |
| 6,623,480 B1 | 9/2003 | Kuo et al. |
| 6,638,278 B2 | 10/2003 | Falwell et al. |
| 6,666,863 B2 | 12/2003 | Wentzel et al. |
| 6,669,693 B2 | 12/2003 | Friedman |
| 6,702,811 B2 | 3/2004 | Stewart et al. |
| 6,719,756 B1 | 4/2004 | Muntermann |
| 6,723,092 B2 | 4/2004 | Brown et al. |
| 6,728,563 B2 | 4/2004 | Rashidi |
| 6,743,225 B2 | 6/2004 | Sanchez et al. |
| 6,743,226 B2 | 6/2004 | Cosman et al. |
| 6,743,239 B1 | 6/2004 | Kuehn et al. |
| 6,764,486 B2 | 7/2004 | Natale |
| 6,780,181 B2 | 8/2004 | Kroll et al. |
| 6,805,128 B1 | 10/2004 | Pless et al. |
| 6,807,447 B2 | 10/2004 | Griffin, III |
| 6,892,091 B1 | 5/2005 | Ben-Haim et al. |
| 6,893,438 B2 | 5/2005 | Hall et al. |
| 6,926,714 B1 | 8/2005 | Sra |
| 6,955,173 B2 | 10/2005 | Lesh |
| 6,960,206 B2 | 11/2005 | Keane |
| 6,960,207 B2 | 11/2005 | Vanney et al. |
| 6,972,016 B2 | 12/2005 | Hill et al. |
| 6,973,339 B2 | 12/2005 | Govari |
| 6,979,331 B2 | 12/2005 | Hintringer et al. |
| 6,984,232 B2 | 1/2006 | Vanney et al. |
| 6,985,776 B2 | 1/2006 | Kane et al. |
| 7,001,383 B2 | 2/2006 | Keidar |
| 7,041,095 B2 | 5/2006 | Wang et al. |
| 7,113,831 B2 | 9/2006 | Hooven |
| 7,171,263 B2 | 1/2007 | Darvish et al. |
| 7,182,725 B2 | 2/2007 | Bonan et al. |
| 7,195,628 B2 | 3/2007 | Falkenberg |
| 7,207,988 B2 | 4/2007 | Leckrone et al. |
| 7,207,989 B2 | 4/2007 | Pike et al. |
| 7,229,402 B2 | 6/2007 | Diaz et al. |
| 7,229,437 B2 | 6/2007 | Johnson et al. |
| 7,250,049 B2 | 7/2007 | Roop et al. |
| 7,285,116 B2 | 10/2007 | De et al. |
| 7,285,119 B2 | 10/2007 | Stewart et al. |
| 7,326,208 B2 | 2/2008 | Vanney et al. |
| 7,346,379 B2 | 3/2008 | Eng et al. |
| 7,367,974 B2 | 5/2008 | Haemmerich et al. |
| 7,374,567 B2 | 5/2008 | Heuser |
| 7,387,629 B2 | 6/2008 | Vanney et al. |

(56) References Cited

U.S. PATENT DOCUMENTS

| | | |
|---|---|---|
| 7,387,630 B2 | 6/2008 | Mest |
| 7,387,636 B2 | 6/2008 | Cohn et al. |
| 7,416,552 B2 | 8/2008 | Paul et al. |
| 7,419,477 B2 | 9/2008 | Simpson et al. |
| 7,419,489 B2 | 9/2008 | Vanney et al. |
| 7,422,591 B2 | 9/2008 | Phan |
| 7,429,261 B2 | 9/2008 | Kunis et al. |
| 7,435,248 B2 | 10/2008 | Taimisto et al. |
| 7,513,896 B2 | 4/2009 | Orszulak |
| 7,527,625 B2 | 5/2009 | Knight et al. |
| 7,578,816 B2 | 8/2009 | Boveja et al. |
| 7,588,567 B2 | 9/2009 | Boveja et al. |
| 7,623,899 B2 | 11/2009 | Worley et al. |
| 7,678,108 B2 | 3/2010 | Chrisitian et al. |
| 7,681,579 B2 | 3/2010 | Schwartz |
| 7,771,421 B2 | 8/2010 | Stewart et al. |
| 7,805,182 B2 | 9/2010 | Weese et al. |
| 7,842,031 B2 | 11/2010 | Abboud et al. |
| 7,850,642 B2 | 12/2010 | Moll et al. |
| 7,850,685 B2 | 12/2010 | Kunis et al. |
| 7,857,808 B2 | 12/2010 | Oral et al. |
| 7,857,809 B2 | 12/2010 | Drysen |
| 7,869,865 B2 | 1/2011 | Govari et al. |
| 7,896,873 B2 | 3/2011 | Hiller et al. |
| 7,917,211 B2 | 3/2011 | Zacouto |
| 7,918,819 B2 | 4/2011 | Karmarkar et al. |
| 7,918,850 B2 | 4/2011 | Govari et al. |
| 7,922,714 B2 | 4/2011 | Stevens-Wright |
| 7,955,827 B2 | 6/2011 | Rubinsky et al. |
| 8,048,067 B2 | 11/2011 | Davalos et al. |
| 8,048,072 B2 | 11/2011 | Verin et al. |
| 8,100,895 B2 | 1/2012 | Panos et al. |
| 8,100,900 B2 | 1/2012 | Prinz et al. |
| 8,108,069 B2 | 1/2012 | Stahler et al. |
| 8,133,220 B2 | 3/2012 | Lee et al. |
| 8,137,342 B2 | 3/2012 | Crossman |
| 8,145,289 B2 | 3/2012 | Calabro' et al. |
| 8,147,486 B2 | 4/2012 | Honour et al. |
| 8,160,690 B2 | 4/2012 | Wilfley et al. |
| 8,175,680 B2 | 5/2012 | Panescu |
| 8,182,477 B2 | 5/2012 | Orszulak et al. |
| 8,206,384 B2 | 6/2012 | Falwell et al. |
| 8,206,385 B2 | 6/2012 | Stangenes et al. |
| 8,216,221 B2 | 7/2012 | Ibrahim et al. |
| 8,221,411 B2 | 7/2012 | Francischelli et al. |
| 8,226,648 B2 | 7/2012 | Paul et al. |
| 8,228,065 B2 | 7/2012 | Wirtz et al. |
| 8,235,986 B2 | 8/2012 | Kulesa et al. |
| 8,235,988 B2 | 8/2012 | Davis et al. |
| 8,251,986 B2 | 8/2012 | Chornenky et al. |
| 8,282,631 B2 | 10/2012 | Davalos et al. |
| 8,287,532 B2 | 10/2012 | Carroll et al. |
| 8,414,508 B2 | 4/2013 | Thapliyal et al. |
| 8,430,875 B2 | 4/2013 | Ibrahim et al. |
| 8,433,394 B2 | 4/2013 | Harlev et al. |
| 8,449,535 B2 | 5/2013 | Deno et al. |
| 8,454,594 B2 | 6/2013 | Demarais et al. |
| 8,463,368 B2 | 6/2013 | Harlev et al. |
| 8,475,450 B2 | 7/2013 | Govari et al. |
| 8,486,063 B2 | 7/2013 | Werneth et al. |
| 8,500,733 B2 | 8/2013 | Watson |
| 8,535,304 B2 | 9/2013 | Sklar et al. |
| 8,538,501 B2 | 9/2013 | Venkatachalam et al. |
| 8,562,588 B2 | 10/2013 | Hobbs et al. |
| 8,568,406 B2 | 10/2013 | Harlev et al. |
| 8,568,410 B2 | 10/2013 | Vakharia et al. |
| 8,571,635 B2 | 10/2013 | McGee |
| 8,571,647 B2 | 10/2013 | Harlev et al. |
| 8,579,897 B2 | 11/2013 | Vakharia et al. |
| 8,585,695 B2 | 11/2013 | Shih |
| 8,588,885 B2 | 11/2013 | Hall et al. |
| 8,597,288 B2 | 12/2013 | Christian |
| 8,608,735 B2 | 12/2013 | Govari et al. |
| 8,628,522 B2 | 1/2014 | Ibrahim et al. |
| 8,632,534 B2 | 1/2014 | Pearson et al. |
| 8,647,338 B2 | 2/2014 | Chornenky et al. |
| 8,708,952 B2 | 4/2014 | Cohen et al. |
| 8,734,442 B2 | 5/2014 | Cao et al. |
| 8,771,267 B2 | 7/2014 | Kunis et al. |
| 8,795,310 B2 | 8/2014 | Fung et al. |
| 8,808,273 B2 | 8/2014 | Caples et al. |
| 8,808,281 B2 | 8/2014 | Emmons et al. |
| 8,834,461 B2 | 9/2014 | Werneth et al. |
| 8,834,464 B2 | 9/2014 | Stewart et al. |
| 8,868,169 B2 | 10/2014 | Narayan et al. |
| 8,876,817 B2 | 11/2014 | Avitall et al. |
| 8,880,195 B2 | 11/2014 | Azure |
| 8,886,309 B2 | 11/2014 | Luther et al. |
| 8,903,488 B2 | 12/2014 | Callas et al. |
| 8,920,411 B2 | 12/2014 | Gelbart et al. |
| 8,926,589 B2 | 1/2015 | Govari |
| 8,932,287 B2 | 1/2015 | Gelbart et al. |
| 8,945,117 B2 | 2/2015 | Bencini |
| 8,979,841 B2 | 3/2015 | Kunis et al. |
| 8,986,278 B2 | 3/2015 | Fung et al. |
| 8,996,091 B2 | 3/2015 | De et al. |
| 9,002,442 B2 | 4/2015 | Harley et al. |
| 9,005,189 B2 | 4/2015 | Davalos et al. |
| 9,005,194 B2 | 4/2015 | Oral et al. |
| 9,011,425 B2 | 4/2015 | Fischer et al. |
| 9,044,245 B2 | 6/2015 | Condie et al. |
| 9,055,959 B2 | 6/2015 | Vaska et al. |
| 9,072,518 B2 | 7/2015 | Swanson |
| 9,078,667 B2 | 7/2015 | Besser et al. |
| 9,101,374 B1 | 8/2015 | Hoch et al. |
| 9,113,911 B2 | 8/2015 | Sherman |
| 9,119,533 B2 | 9/2015 | Ghaffari |
| 9,119,634 B2 | 9/2015 | Gelbart et al. |
| 9,131,897 B2 | 9/2015 | Harada et al. |
| 9,155,590 B2 | 10/2015 | Mathur |
| 9,162,037 B2 | 10/2015 | Belson et al. |
| 9,179,972 B2 | 11/2015 | Olson |
| 9,186,481 B2 | 11/2015 | Avitall et al. |
| 9,192,769 B2 | 11/2015 | Donofrio et al. |
| 9,204,916 B2 | 12/2015 | Lalonde |
| 9,211,405 B2 | 12/2015 | Mahapatra et al. |
| 9,216,055 B2 | 12/2015 | Spence et al. |
| 9,233,248 B2 | 1/2016 | Luther et al. |
| 9,237,926 B2 | 1/2016 | Nollert et al. |
| 9,262,252 B2 | 2/2016 | Kirkpatrick et al. |
| 9,277,957 B2 | 3/2016 | Long et al. |
| 9,282,910 B2 | 3/2016 | Narayan et al. |
| 9,289,258 B2 | 3/2016 | Cohen |
| 9,289,606 B2 | 3/2016 | Paul et al. |
| 9,295,516 B2 | 3/2016 | Pearson et al. |
| 9,301,801 B2 | 4/2016 | Scheib |
| 9,351,789 B2 | 5/2016 | Novichenok et al. |
| 9,375,268 B2 | 6/2016 | Long |
| 9,387,031 B2 | 7/2016 | Stewart et al. |
| 9,414,881 B2 | 8/2016 | Callas et al. |
| 9,468,495 B2 | 10/2016 | Kunis et al. |
| 9,474,486 B2 | 10/2016 | Eliason et al. |
| 9,474,574 B2 | 10/2016 | Ibrahim et al. |
| 9,480,525 B2 | 11/2016 | Lopes et al. |
| 9,486,272 B2 | 11/2016 | Bonyak et al. |
| 9,486,273 B2 | 11/2016 | Lopes et al. |
| 9,492,227 B2 | 11/2016 | Lopes et al. |
| 9,492,228 B2 | 11/2016 | Lopes et al. |
| 9,510,888 B2 | 12/2016 | Lalonde |
| 9,517,103 B2 | 12/2016 | Panescu et al. |
| 9,526,573 B2 | 12/2016 | Lopes et al. |
| 9,532,831 B2 | 1/2017 | Reinders et al. |
| 9,539,010 B2 | 1/2017 | Gagner et al. |
| 9,554,848 B2 | 1/2017 | Stewart et al. |
| 9,554,851 B2 | 1/2017 | Sklar et al. |
| 9,700,368 B2 | 7/2017 | Callas et al. |
| 9,724,170 B2 | 8/2017 | Mickelsen |
| 9,757,193 B2 | 9/2017 | Zarins et al. |
| 9,782,099 B2 | 10/2017 | Williams et al. |
| 9,795,442 B2 | 10/2017 | Salahieh et al. |
| 9,801,681 B2 | 10/2017 | Laske et al. |
| 9,808,304 B2 | 11/2017 | Lalonde |
| 9,861,802 B2 | 1/2018 | Mickelsen |
| 9,913,685 B2 | 3/2018 | Clark et al. |

(56) References Cited

U.S. PATENT DOCUMENTS

| | | |
|---|---|---|
| 9,931,487 B2 | 4/2018 | Quinn et al. |
| 9,987,081 B1 | 6/2018 | Bowers et al. |
| 9,999,465 B2 | 6/2018 | Long et al. |
| 10,010,368 B2 | 7/2018 | Laske et al. |
| 10,016,232 B1 | 7/2018 | Bowers et al. |
| 10,130,423 B1 | 11/2018 | Viswanathan et al. |
| 10,172,673 B2 | 1/2019 | Viswanathan et al. |
| 10,194,818 B2 | 2/2019 | Williams et al. |
| 10,285,755 B2 | 5/2019 | Stewart et al. |
| 10,322,286 B2 | 6/2019 | Viswanathan et al. |
| 10,433,906 B2 | 10/2019 | Mickelsen |
| 10,433,908 B2 | 10/2019 | Viswanathan et al. |
| 10,512,505 B2 | 12/2019 | Viswanathan |
| 10,512,779 B2 | 12/2019 | Viswanathan et al. |
| 10,517,672 B2 | 12/2019 | Long |
| 10,617,467 B2 | 4/2020 | Viswanathan et al. |
| 10,660,702 B2 | 5/2020 | Viswanathan et al. |
| 2001/0000791 A1 | 5/2001 | Suorsa et al. |
| 2001/0007070 A1 | 7/2001 | Stewart et al. |
| 2001/0044624 A1 | 11/2001 | Seraj et al. |
| 2002/0022839 A1 | 2/2002 | Stewart et al. |
| 2002/0052602 A1 | 5/2002 | Wang et al. |
| 2002/0058933 A1 | 5/2002 | Christopherson et al. |
| 2002/0077627 A1 | 6/2002 | Johnson et al. |
| 2002/0087169 A1 | 7/2002 | Brock et al. |
| 2002/0091384 A1 | 7/2002 | Hooven et al. |
| 2002/0095176 A1 | 7/2002 | Prestel |
| 2002/0111618 A1 | 8/2002 | Stewart et al. |
| 2002/0156526 A1 | 10/2002 | Hlavka et al. |
| 2002/0161323 A1 | 10/2002 | Miller et al. |
| 2002/0169445 A1 | 11/2002 | Jain et al. |
| 2002/0177765 A1 | 11/2002 | Bowe et al. |
| 2002/0183638 A1 | 12/2002 | Swanson |
| 2003/0014098 A1 | 1/2003 | Quijano et al. |
| 2003/0018374 A1 | 1/2003 | Paulos |
| 2003/0023287 A1 | 1/2003 | Edwards et al. |
| 2003/0028189 A1 | 2/2003 | Woloszko et al. |
| 2003/0050637 A1 | 3/2003 | Maguire et al. |
| 2003/0060856 A1 | 3/2003 | Chornenky et al. |
| 2003/0114849 A1 | 6/2003 | Ryan |
| 2003/0125729 A1 | 7/2003 | Hooven et al. |
| 2003/0130598 A1 | 7/2003 | Manning et al. |
| 2003/0130711 A1 | 7/2003 | Pearson et al. |
| 2003/0204161 A1 | 10/2003 | Ferek-Petric |
| 2003/0229379 A1 | 12/2003 | Ramsey |
| 2004/0039382 A1 | 2/2004 | Kroll et al. |
| 2004/0049181 A1 | 3/2004 | Stewart et al. |
| 2004/0049182 A1 | 3/2004 | Koblish et al. |
| 2004/0082859 A1 | 4/2004 | Schaer |
| 2004/0082948 A1 | 4/2004 | Stewart et al. |
| 2004/0087939 A1 | 5/2004 | Eggers et al. |
| 2004/0111087 A1 | 6/2004 | Stern et al. |
| 2004/0199157 A1 | 10/2004 | Palanker et al. |
| 2004/0231683 A1 | 11/2004 | Eng et al. |
| 2004/0236360 A1 | 11/2004 | Cohn et al. |
| 2004/0254607 A1 | 12/2004 | Wittenberger et al. |
| 2004/0267337 A1 | 12/2004 | Hayzelden |
| 2005/0033282 A1 | 2/2005 | Hooven |
| 2005/0187545 A1 | 8/2005 | Hooven et al. |
| 2005/0222632 A1 | 10/2005 | Obino |
| 2005/0251130 A1 | 11/2005 | Boveja et al. |
| 2005/0261672 A1 | 11/2005 | Deem et al. |
| 2006/0009755 A1 | 1/2006 | Sra |
| 2006/0009759 A1 | 1/2006 | Christian et al. |
| 2006/0015095 A1 | 1/2006 | Desinger et al. |
| 2006/0015165 A1 | 1/2006 | Bertolero et al. |
| 2006/0024359 A1 | 2/2006 | Walker et al. |
| 2006/0058781 A1 | 3/2006 | Long |
| 2006/0111702 A1 | 5/2006 | Oral et al. |
| 2006/0142801 A1 | 6/2006 | Demarais et al. |
| 2006/0161148 A1* | 7/2006 | Behnke ............ A61B 18/1206 606/34 |
| 2006/0167448 A1 | 7/2006 | Kozel |
| 2006/0217703 A1 | 9/2006 | Chornenky et al. |
| 2006/0241734 A1 | 10/2006 | Marshall et al. |
| 2006/0264752 A1 | 11/2006 | Rubinsky et al. |
| 2006/0270900 A1 | 11/2006 | Chin et al. |
| 2006/0287648 A1 | 12/2006 | Schwartz |
| 2006/0293730 A1 | 12/2006 | Rubinsky et al. |
| 2006/0293731 A1 | 12/2006 | Rubinsky et al. |
| 2007/0005053 A1 | 1/2007 | Dando |
| 2007/0021744 A1 | 1/2007 | Creighton |
| 2007/0060989 A1 | 3/2007 | Deem et al. |
| 2007/0066972 A1 | 3/2007 | Ormsby et al. |
| 2007/0129721 A1 | 6/2007 | Phan et al. |
| 2007/0129760 A1 | 6/2007 | Demarais et al. |
| 2007/0156135 A1 | 7/2007 | Rubinsky et al. |
| 2007/0167740 A1 | 7/2007 | Grunewald et al. |
| 2007/0167940 A1 | 7/2007 | Stevens-Wright |
| 2007/0173878 A1 | 7/2007 | Heuser |
| 2007/0208329 A1 | 9/2007 | Ward et al. |
| 2007/0225589 A1 | 9/2007 | Viswanathan |
| 2007/0249923 A1 | 10/2007 | Keenan |
| 2007/0260223 A1 | 11/2007 | Scheibe et al. |
| 2007/0270792 A1 | 11/2007 | Hennemann et al. |
| 2008/0009855 A1 | 1/2008 | Hamou |
| 2008/0033426 A1 | 2/2008 | Machell |
| 2008/0065061 A1 | 3/2008 | Viswanathan |
| 2008/0086120 A1 | 4/2008 | Mirza et al. |
| 2008/0091195 A1 | 4/2008 | Sliwa et al. |
| 2008/0103545 A1 | 5/2008 | Bolea et al. |
| 2008/0132885 A1 | 6/2008 | Rubinsky et al. |
| 2008/0161789 A1 | 7/2008 | Thao et al. |
| 2008/0172048 A1 | 7/2008 | Martin et al. |
| 2008/0200913 A1 | 8/2008 | Viswanathan |
| 2008/0208118 A1 | 8/2008 | Goldman |
| 2008/0243214 A1 | 10/2008 | Koblish |
| 2008/0281322 A1 | 11/2008 | Sherman et al. |
| 2008/0300574 A1 | 12/2008 | Belson et al. |
| 2008/0300588 A1 | 12/2008 | Groth et al. |
| 2009/0024084 A1 | 1/2009 | Khosla et al. |
| 2009/0048591 A1 | 2/2009 | Ibrahim et al. |
| 2009/0062788 A1 | 3/2009 | Long et al. |
| 2009/0076496 A1 | 3/2009 | Azure |
| 2009/0076500 A1 | 3/2009 | Azure |
| 2009/0105654 A1 | 4/2009 | Kurth et al. |
| 2009/0138009 A1 | 5/2009 | Viswanathan et al. |
| 2009/0149917 A1 | 6/2009 | Whitehurst et al. |
| 2009/0163905 A1 | 6/2009 | Winkler et al. |
| 2009/0228003 A1 | 9/2009 | Sinelnikov |
| 2009/0240248 A1 | 9/2009 | Deford et al. |
| 2009/0275827 A1 | 11/2009 | Aiken et al. |
| 2009/0281477 A1 | 11/2009 | Mikus et al. |
| 2009/0306651 A1 | 12/2009 | Schneider |
| 2010/0004623 A1 | 1/2010 | Hamilton et al. |
| 2010/0023004 A1 | 1/2010 | Francischelli et al. |
| 2010/0137861 A1 | 6/2010 | Soroff et al. |
| 2010/0185140 A1 | 7/2010 | Kassab et al. |
| 2010/0185186 A1 | 7/2010 | Longoria |
| 2010/0191112 A1 | 7/2010 | Demarais et al. |
| 2010/0191232 A1 | 7/2010 | Boveda |
| 2010/0241185 A1 | 9/2010 | Mahapatra et al. |
| 2010/0261994 A1 | 10/2010 | Davalos et al. |
| 2010/0274238 A1 | 10/2010 | Klimovitch |
| 2010/0280513 A1 | 11/2010 | Juergen et al. |
| 2010/0280539 A1 | 11/2010 | Miyoshi et al. |
| 2010/0292687 A1 | 11/2010 | Kauphusman et al. |
| 2010/0312096 A1 | 12/2010 | Guttman et al. |
| 2010/0312300 A1 | 12/2010 | Ryu et al. |
| 2011/0028962 A1 | 2/2011 | Werneth et al. |
| 2011/0028964 A1 | 2/2011 | Edwards |
| 2011/0040199 A1 | 2/2011 | Hopenfeld |
| 2011/0098694 A1 | 4/2011 | Long |
| 2011/0106221 A1 | 5/2011 | Neal et al. |
| 2011/0130708 A1 | 6/2011 | Perry et al. |
| 2011/0144524 A1 | 6/2011 | Fish et al. |
| 2011/0144633 A1 | 6/2011 | Govari |
| 2011/0160785 A1 | 6/2011 | Mori et al. |
| 2011/0190659 A1 | 8/2011 | Long et al. |
| 2011/0190727 A1 | 8/2011 | Edmunds et al. |
| 2011/0213231 A1 | 9/2011 | Hall et al. |
| 2011/0276047 A1 | 11/2011 | Sklar et al. |
| 2011/0276075 A1 | 11/2011 | Fung et al. |
| 2011/0288544 A1 | 11/2011 | Verin et al. |

(56) References Cited

U.S. PATENT DOCUMENTS

| | | |
|---|---|---|
| 2011/0288547 A1 | 11/2011 | Morgan et al. |
| 2011/0313417 A1 | 12/2011 | De et al. |
| 2012/0029512 A1 | 2/2012 | Willard et al. |
| 2012/0046570 A1 | 2/2012 | Villegas et al. |
| 2012/0053581 A1 | 3/2012 | Wittkampf et al. |
| 2012/0059255 A1 | 3/2012 | Paul et al. |
| 2012/0071872 A1 | 3/2012 | Rubinsky et al. |
| 2012/0078320 A1 | 3/2012 | Schotzko et al. |
| 2012/0078343 A1 | 3/2012 | Fish |
| 2012/0089089 A1 | 4/2012 | Swain et al. |
| 2012/0095459 A1 | 4/2012 | Callas et al. |
| 2012/0101413 A1 | 4/2012 | Beetel et al. |
| 2012/0158021 A1 | 6/2012 | Morrill |
| 2012/0165667 A1 | 6/2012 | Altmann et al. |
| 2012/0172859 A1 | 7/2012 | Condie et al. |
| 2012/0172867 A1 | 7/2012 | Ryu et al. |
| 2012/0197100 A1 | 8/2012 | Razavi et al. |
| 2012/0209260 A1 | 8/2012 | Lambert et al. |
| 2012/0220998 A1 | 8/2012 | Long et al. |
| 2012/0265198 A1 | 10/2012 | Crow et al. |
| 2012/0283582 A1 | 11/2012 | Mahapatra et al. |
| 2012/0303019 A1 | 11/2012 | Zhao et al. |
| 2012/0310052 A1 | 12/2012 | Mahapatra et al. |
| 2012/0310230 A1 | 12/2012 | Willis |
| 2012/0310237 A1 | 12/2012 | Swanson |
| 2012/0316557 A1 | 12/2012 | Sartor et al. |
| 2013/0030430 A1 | 1/2013 | Stewart et al. |
| 2013/0060247 A1 | 3/2013 | Sklar et al. |
| 2013/0060248 A1 | 3/2013 | Sklar et al. |
| 2013/0079768 A1 | 3/2013 | De et al. |
| 2013/0090651 A1 | 4/2013 | Smith |
| 2013/0096655 A1 | 4/2013 | Moffitt et al. |
| 2013/0103027 A1 | 4/2013 | Sklar et al. |
| 2013/0103064 A1 | 4/2013 | Arenson et al. |
| 2013/0131662 A1 | 5/2013 | Wittkampf |
| 2013/0158538 A1 | 6/2013 | Govari |
| 2013/0158621 A1 | 6/2013 | Ding et al. |
| 2013/0172715 A1 | 7/2013 | Just et al. |
| 2013/0172864 A1 | 7/2013 | Ibrahim et al. |
| 2013/0172875 A1 | 7/2013 | Govari et al. |
| 2013/0184702 A1 | 7/2013 | Neal et al. |
| 2013/0218157 A1 | 8/2013 | Callas et al. |
| 2013/0226174 A1 | 8/2013 | Ibrahim et al. |
| 2013/0237984 A1 | 9/2013 | Sklar |
| 2013/0253415 A1 | 9/2013 | Sano et al. |
| 2013/0296679 A1 | 11/2013 | Condie et al. |
| 2013/0310829 A1 | 11/2013 | Cohen |
| 2013/0317385 A1 | 11/2013 | Sklar et al. |
| 2013/0331831 A1 | 12/2013 | Werneth et al. |
| 2013/0338467 A1 | 12/2013 | Grasse et al. |
| 2014/0005664 A1 | 1/2014 | Govari et al. |
| 2014/0024911 A1 | 1/2014 | Harlev et al. |
| 2014/0039288 A1 | 2/2014 | Hue-Teh |
| 2014/0051993 A1 | 2/2014 | McGee |
| 2014/0052118 A1 | 2/2014 | Laske et al. |
| 2014/0052126 A1 | 2/2014 | Long et al. |
| 2014/0052216 A1 | 2/2014 | Long et al. |
| 2014/0058377 A1 | 2/2014 | Deem et al. |
| 2014/0081113 A1 | 3/2014 | Cohen et al. |
| 2014/0100563 A1 | 4/2014 | Govari et al. |
| 2014/0107644 A1 | 4/2014 | Falwell et al. |
| 2014/0142408 A1 | 5/2014 | De et al. |
| 2014/0148804 A1 | 5/2014 | Ward et al. |
| 2014/0163480 A1 | 6/2014 | Govari et al. |
| 2014/0163546 A1 | 6/2014 | Govari et al. |
| 2014/0171942 A1 | 6/2014 | Werneth et al. |
| 2014/0180035 A1 | 6/2014 | Anderson |
| 2014/0187916 A1 | 7/2014 | Clark et al. |
| 2014/0194716 A1 | 7/2014 | Diep et al. |
| 2014/0194867 A1 | 7/2014 | Fish et al. |
| 2014/0200567 A1 | 7/2014 | Cox et al. |
| 2014/0235986 A1 | 8/2014 | Harlev et al. |
| 2014/0235988 A1 | 8/2014 | Ghosh |
| 2014/0235989 A1 | 8/2014 | Wodlinger et al. |
| 2014/0243851 A1 | 8/2014 | Cohen et al. |
| 2014/0253140 A1 | 9/2014 | Gilbert |
| 2014/0276760 A1 | 9/2014 | Bonyak et al. |
| 2014/0276782 A1 | 9/2014 | Paskar |
| 2014/0276791 A1 | 9/2014 | Ku et al. |
| 2014/0288556 A1 | 9/2014 | Ibrahim et al. |
| 2014/0303721 A1 | 10/2014 | Fung et al. |
| 2014/0343549 A1 | 11/2014 | Spear et al. |
| 2014/0364797 A1* | 12/2014 | Schoenbach ....... A61B 18/1206 606/41 |
| 2014/0364845 A1 | 12/2014 | Rashidi |
| 2014/0371613 A1 | 12/2014 | Narayan et al. |
| 2015/0005767 A1 | 1/2015 | Werneth et al. |
| 2015/0011995 A1 | 1/2015 | Avitall et al. |
| 2015/0066108 A1 | 3/2015 | Shi et al. |
| 2015/0119674 A1 | 4/2015 | Fischell et al. |
| 2015/0126840 A1 | 5/2015 | Thakur et al. |
| 2015/0133914 A1 | 5/2015 | Koblish |
| 2015/0138977 A1 | 5/2015 | Dacosta |
| 2015/0141978 A1 | 5/2015 | Subramaniam et al. |
| 2015/0141982 A1 | 5/2015 | Lee |
| 2015/0142041 A1 | 5/2015 | Kendale et al. |
| 2015/0148796 A1 | 5/2015 | Bencini |
| 2015/0150472 A1 | 6/2015 | Harlev et al. |
| 2015/0157402 A1 | 6/2015 | Kunis et al. |
| 2015/0157412 A1 | 6/2015 | Wallace et al. |
| 2015/0164584 A1 | 6/2015 | Davalos et al. |
| 2015/0173824 A1 | 6/2015 | Davalos et al. |
| 2015/0173828 A1 | 6/2015 | Avitall |
| 2015/0174404 A1 | 6/2015 | Rousso et al. |
| 2015/0182740 A1 | 7/2015 | Mickelsen |
| 2015/0196217 A1 | 7/2015 | Harlev et al. |
| 2015/0223726 A1 | 8/2015 | Harlev et al. |
| 2015/0230699 A1 | 8/2015 | Berul et al. |
| 2015/0258344 A1 | 9/2015 | Tandri et al. |
| 2015/0265342 A1 | 9/2015 | Long et al. |
| 2015/0265344 A1 | 9/2015 | Aktas et al. |
| 2015/0272656 A1 | 10/2015 | Chen |
| 2015/0272664 A9 | 10/2015 | Cohen |
| 2015/0272667 A1 | 10/2015 | Govari et al. |
| 2015/0282729 A1 | 10/2015 | Harlev et al. |
| 2015/0289923 A1 | 10/2015 | Davalos et al. |
| 2015/0304879 A1 | 10/2015 | Dacosta |
| 2015/0320481 A1 | 11/2015 | Cosman et al. |
| 2015/0321021 A1 | 11/2015 | Tandri et al. |
| 2015/0342532 A1 | 12/2015 | Basu et al. |
| 2015/0343212 A1 | 12/2015 | Rousso et al. |
| 2015/0351836 A1 | 12/2015 | Prutchi |
| 2015/0359583 A1 | 12/2015 | Swanson |
| 2016/0000500 A1 | 1/2016 | Salahieh et al. |
| 2016/0008061 A1 | 1/2016 | Fung et al. |
| 2016/0008065 A1 | 1/2016 | Gliner et al. |
| 2016/0029960 A1 | 2/2016 | Toth et al. |
| 2016/0038772 A1 | 2/2016 | Thapliyal et al. |
| 2016/0051204 A1 | 2/2016 | Harlev et al. |
| 2016/0051324 A1 | 2/2016 | Stewart et al. |
| 2016/0058493 A1 | 3/2016 | Neal et al. |
| 2016/0058506 A1 | 3/2016 | Spence et al. |
| 2016/0066993 A1 | 3/2016 | Avitall et al. |
| 2016/0074679 A1 | 3/2016 | Thapliyal et al. |
| 2016/0095531 A1 | 4/2016 | Narayan et al. |
| 2016/0095642 A1 | 4/2016 | Deno et al. |
| 2016/0095653 A1 | 4/2016 | Lambert et al. |
| 2016/0100797 A1 | 4/2016 | Mahapatra et al. |
| 2016/0100879 A1 | 4/2016 | Long |
| 2016/0100884 A1 | 4/2016 | Fay et al. |
| 2016/0106498 A1 | 4/2016 | Highsmith et al. |
| 2016/0106500 A1 | 4/2016 | Olson |
| 2016/0113709 A1 | 4/2016 | Maor |
| 2016/0113712 A1 | 4/2016 | Cheung et al. |
| 2016/0120564 A1 | 5/2016 | Kirkpatrick et al. |
| 2016/0128770 A1 | 5/2016 | Afonso et al. |
| 2016/0166167 A1 | 6/2016 | Narayan et al. |
| 2016/0166310 A1 | 6/2016 | Stewart et al. |
| 2016/0166311 A1 | 6/2016 | Long et al. |
| 2016/0174865 A1 | 6/2016 | Stewart et al. |
| 2016/0183877 A1 | 6/2016 | Williams et al. |
| 2016/0184003 A1 | 6/2016 | Srimathveeravalli et al. |
| 2016/0184004 A1 | 6/2016 | Hull et al. |
| 2016/0213282 A1 | 7/2016 | Leo et al. |

(56) References Cited

U.S. PATENT DOCUMENTS

| | | |
|---|---|---|
| 2016/0220307 A1 | 8/2016 | Miller et al. |
| 2016/0235470 A1 | 8/2016 | Callas et al. |
| 2016/0249972 A1 | 9/2016 | Klink |
| 2016/0256682 A1 | 9/2016 | Paul et al. |
| 2016/0287314 A1 | 10/2016 | Arena et al. |
| 2016/0310211 A1 | 10/2016 | Long |
| 2016/0324564 A1 | 11/2016 | Gerlach et al. |
| 2016/0324573 A1 | 11/2016 | Mickelson et al. |
| 2016/0331441 A1 | 11/2016 | Konings |
| 2016/0331459 A1 | 11/2016 | Townley et al. |
| 2016/0338770 A1 | 11/2016 | Bar-Tal et al. |
| 2016/0354142 A1 | 12/2016 | Pearson et al. |
| 2016/0361109 A1 | 12/2016 | Weaver et al. |
| 2017/0001016 A1 | 1/2017 | De Ridder |
| 2017/0035499 A1 | 2/2017 | Stewart et al. |
| 2017/0042449 A1 | 2/2017 | Deno et al. |
| 2017/0042615 A1 | 2/2017 | Salahieh et al. |
| 2017/0056648 A1 | 3/2017 | Syed et al. |
| 2017/0065330 A1 | 3/2017 | Mickelson et al. |
| 2017/0065339 A1 | 3/2017 | Mickelson |
| 2017/0065340 A1 | 3/2017 | Long |
| 2017/0065343 A1 | 3/2017 | Mickelson |
| 2017/0071543 A1 | 3/2017 | Basu et al. |
| 2017/0095291 A1 | 4/2017 | Harrington et al. |
| 2017/0105793 A1 | 4/2017 | Cao et al. |
| 2017/0120048 A1 | 5/2017 | He et al. |
| 2017/0146584 A1 | 5/2017 | Daw et al. |
| 2017/0151014 A1 | 6/2017 | Perfler |
| 2017/0151029 A1 | 6/2017 | Mickelson |
| 2017/0172654 A1 | 6/2017 | Wittkampf et al. |
| 2017/0181795 A1 | 6/2017 | Debruyne |
| 2017/0189097 A1 | 7/2017 | Viswanathan et al. |
| 2017/0215953 A1 | 8/2017 | Long et al. |
| 2017/0245928 A1 | 8/2017 | Xiao et al. |
| 2017/0246455 A1 | 8/2017 | Athos et al. |
| 2017/0312024 A1 | 11/2017 | Harlev et al. |
| 2017/0312025 A1 | 11/2017 | Harlev et al. |
| 2017/0312027 A1 | 11/2017 | Harlev et al. |
| 2017/0319851 A1* | 11/2017 | Athos ................ H03H 11/28 |
| 2018/0001056 A1 | 1/2018 | Leeflang et al. |
| 2018/0028252 A1 | 2/2018 | Lalonde |
| 2018/0042674 A1 | 2/2018 | Mickelsen |
| 2018/0042675 A1 | 2/2018 | Long |
| 2018/0043153 A1 | 2/2018 | Viswanathan et al. |
| 2018/0064488 A1 | 3/2018 | Long et al. |
| 2018/0085160 A1 | 3/2018 | Viswanathan et al. |
| 2018/0093088 A1 | 4/2018 | Mickelsen |
| 2018/0133460 A1 | 5/2018 | Townley et al. |
| 2018/0161093 A1 | 6/2018 | Basu et al. |
| 2018/0168511 A1 | 6/2018 | Hall et al. |
| 2018/0184982 A1 | 7/2018 | Basu et al. |
| 2018/0193090 A1 | 7/2018 | De et al. |
| 2018/0200497 A1 | 7/2018 | Mickelsen |
| 2018/0235496 A1 | 8/2018 | Wu et al. |
| 2018/0256109 A1 | 9/2018 | Wu et al. |
| 2018/0280080 A1 | 10/2018 | Govari et al. |
| 2018/0303488 A1 | 10/2018 | Hill |
| 2018/0303543 A1 | 10/2018 | Stewart et al. |
| 2018/0311497 A1 | 11/2018 | Viswanathan et al. |
| 2018/0344202 A1 | 12/2018 | Bar-Tal et al. |
| 2018/0344393 A1 | 12/2018 | Gruba et al. |
| 2018/0360531 A1 | 12/2018 | Holmes et al. |
| 2018/0360534 A1 | 12/2018 | Teplitsky et al. |
| 2019/0015007 A1 | 1/2019 | Rottmann et al. |
| 2019/0015638 A1 | 1/2019 | Gruba et al. |
| 2019/0030328 A1 | 1/2019 | Stewart et al. |
| 2019/0046791 A1 | 2/2019 | Ebbers et al. |
| 2019/0069950 A1 | 3/2019 | Viswanathan et al. |
| 2019/0076179 A1 | 3/2019 | Babkin et al. |
| 2019/0125439 A1 | 5/2019 | Rohl et al. |
| 2019/0125788 A1 | 5/2019 | Gruba et al. |
| 2019/0143106 A1 | 5/2019 | Dewitt et al. |
| 2019/0151015 A1 | 5/2019 | Viswanathan et al. |
| 2019/0175263 A1 | 6/2019 | Altmann et al. |
| 2019/0183378 A1 | 6/2019 | Mosesov et al. |
| 2019/0183567 A1 | 6/2019 | Govari et al. |
| 2019/0192223 A1 | 6/2019 | Rankin |
| 2019/0201089 A1 | 7/2019 | Waldstreicher et al. |
| 2019/0201688 A1 | 7/2019 | Olson |
| 2019/0209235 A1 | 7/2019 | Stewart et al. |
| 2019/0223948 A1 | 7/2019 | Stewart et al. |
| 2019/0231421 A1 | 8/2019 | Viswanathan et al. |
| 2019/0231425 A1 | 8/2019 | Waldstreicher et al. |
| 2019/0254735 A1 | 8/2019 | Stewart et al. |
| 2019/0269912 A1 | 9/2019 | Viswanathan et al. |
| 2019/0298442 A1 | 10/2019 | Ogata et al. |
| 2019/0307500 A1 | 10/2019 | Byrd et al. |
| 2019/0350647 A1 | 11/2019 | Ramberg et al. |
| 2019/0350649 A1 | 11/2019 | Sutermeister et al. |
| 2020/0008869 A1 | 1/2020 | Byrd |
| 2020/0008870 A1 | 1/2020 | Gruba et al. |
| 2020/0009378 A1 | 1/2020 | Stewart et al. |
| 2020/0038104 A1 | 2/2020 | Mickelsen |
| 2020/0046423 A1 | 2/2020 | Viswanathan et al. |
| 2020/0093539 A1 | 3/2020 | Long et al. |
| 2020/0129233 A1* | 4/2020 | Viswanathan ..... A61B 18/1492 |
| 2020/0289827 A1 | 9/2020 | Forsyth et al. |
| 2021/0393327 A1* | 12/2021 | Eyster ................ A61B 18/1815 |
| 2022/0133405 A1 | 5/2022 | Mickelsen |

FOREIGN PATENT DOCUMENTS

| | | |
|---|---|---|
| EP | 1125549 A2 | 8/2001 |
| EP | 0797956 B1 | 6/2003 |
| EP | 1340469 A1 | 9/2003 |
| EP | 1127552 B1 | 6/2006 |
| EP | 1803411 A2 | 7/2007 |
| EP | 1009303 B1 | 6/2009 |
| EP | 2213729 A2 | 8/2010 |
| EP | 2382935 A1 | 11/2011 |
| EP | 2425871 A2 | 3/2012 |
| EP | 2532320 A2 | 12/2012 |
| EP | 2587275 A1 | 5/2013 |
| EP | 2663227 A1 | 11/2013 |
| EP | 1909678 B1 | 1/2014 |
| EP | 2217165 B1 | 3/2014 |
| EP | 2376193 B1 | 3/2014 |
| EP | 2708181 A1 | 3/2014 |
| EP | 2777579 A1 | 9/2014 |
| EP | 2777585 A1 | 9/2014 |
| EP | 2934307 A1 | 10/2015 |
| EP | 3056242 A1 | 8/2016 |
| EP | 3111871 A1 | 1/2017 |
| EP | 3151773 B1 | 4/2018 |
| JP | 06-507797 A | 9/1994 |
| JP | 2000-508196 A | 7/2000 |
| JP | 2005-516666 A | 6/2005 |
| JP | 2006-506184 A | 2/2006 |
| JP | 2008-538997 A | 11/2008 |
| JP | 2009-500129 A | 1/2009 |
| JP | 2011-509158 A | 3/2011 |
| JP | 2012-050538 A | 3/2012 |
| JP | 2018-510015 A | 4/2018 |
| JP | 2018-089431 A | 6/2018 |
| JP | 2020-516371 A | 6/2020 |
| WO | 92/07622 A1 | 5/1992 |
| WO | 92/21278 A1 | 12/1992 |
| WO | 92/21285 A1 | 12/1992 |
| WO | 94/07413 A1 | 4/1994 |
| WO | 97/24073 A1 | 7/1997 |
| WO | 97/25917 A1 | 7/1997 |
| WO | 97/37719 A1 | 10/1997 |
| WO | 99/04851 A1 | 2/1999 |
| WO | 99/22659 A1 | 5/1999 |
| WO | 99/56650 A1 | 11/1999 |
| WO | 99/59486 A2 | 11/1999 |
| WO | 02/56782 A2 | 7/2002 |
| WO | 03/53289 A1 | 7/2003 |
| WO | 03/65916 A1 | 8/2003 |
| WO | 2004/045442 A1 | 6/2004 |
| WO | 2004/086994 A1 | 10/2004 |
| WO | 2005/046487 A1 | 5/2005 |
| WO | 2006/115902 A2 | 11/2006 |
| WO | 2007/006055 A2 | 1/2007 |

(56) References Cited

FOREIGN PATENT DOCUMENTS

| | | |
|---|---|---|
| WO | 2007/079438 A2 | 7/2007 |
| WO | 2009/082710 A1 | 7/2009 |
| WO | 2009/089343 A1 | 7/2009 |
| WO | 2009/137800 A2 | 11/2009 |
| WO | 2010/014480 A1 | 2/2010 |
| WO | 2011/028310 A1 | 3/2011 |
| WO | 2011/154805 A1 | 12/2011 |
| WO | 2012/051433 A2 | 4/2012 |
| WO | 2012/097067 A1 | 7/2012 |
| WO | 2012/153928 A2 | 11/2012 |
| WO | 2013/019385 A1 | 2/2013 |
| WO | 2014/025394 A1 | 2/2014 |
| WO | 2014/031800 A1 | 2/2014 |
| WO | 2014/036439 A2 | 3/2014 |
| WO | 2014/100579 A1 | 6/2014 |
| WO | 2014/160832 A2 | 10/2014 |
| WO | 2015/066322 A1 | 5/2015 |
| WO | 2015/099786 A1 | 7/2015 |
| WO | 2015/103530 A1 | 7/2015 |
| WO | 2015/103574 A1 | 7/2015 |
| WO | 2015/130824 A1 | 9/2015 |
| WO | 2015/140741 A1 | 9/2015 |
| WO | 2015/143327 A1 | 9/2015 |
| WO | 2015/171921 A2 | 11/2015 |
| WO | 2015/175944 A1 | 11/2015 |
| WO | 2015/192018 A1 | 12/2015 |
| WO | 2015/192027 A1 | 12/2015 |
| WO | 2016/059027 A1 | 4/2016 |
| WO | 2016/060983 A1 | 4/2016 |
| WO | 2016/081650 A1 | 5/2016 |
| WO | 2016/090175 A1 | 6/2016 |
| WO | 2017/093926 A1 | 6/2017 |
| WO | 2017/119934 A1 | 7/2017 |
| WO | 2017/120169 A1 | 7/2017 |
| WO | 2017/192477 A1 | 11/2017 |
| WO | 2017/192495 A1 | 11/2017 |
| WO | 2017/201504 A1 | 11/2017 |
| WO | 2017/218734 A1 | 12/2017 |
| WO | 2018/005511 A1 | 1/2018 |
| WO | 2018/106569 A1 | 6/2018 |
| WO | 2018/200800 A1 | 11/2018 |
| WO | 2019/023259 A2 | 1/2019 |
| WO | 2019/023280 A1 | 1/2019 |
| WO | 2019/035071 A1 | 2/2019 |
| WO | 2019/133606 A1 | 7/2019 |
| WO | 2019/133608 A1 | 7/2019 |
| WO | 2019/136218 A1 | 7/2019 |
| WO | 2019/181612 A1 | 9/2019 |
| WO | 2019/234133 A1 | 12/2019 |

OTHER PUBLICATIONS

Hobbs, E. P., "Investor Relations Update: Tissue Ablation via Irreversible Electroporation (IRE)," Powerpoint (2004), 16 pages.
International Search Report and Written Opinion received for PCT Patent Application No. PCT/US2022/013512, mailed on May 4, 2022, 12 pages.
Lavee, J. et al., "A Novel Nonthermal Energy Source for Surgical Epicardial Atrial Ablation: Irreversible Electroporation," The Heart Surgery Forum #2006-1202, 10(2), 2007 [Epub Mar. 2007].
Madhavan, M. et al., "Novel Percutaneous Epicardial Autonomic Modulation in the Canine for Atrial Fibrillation: Results of an Efficacy and Safety Study," Pace, 00:1-11 (2016).
Neven, K. et al., "Epicardial linear electroporation ablation and lesion size," Heart Rhythm, 11:1465-1470 (2014).
Neven, K. et al., "Myocardial Lesion Size After Epicardial Electroporation Catheter Ablation After Subxiphoid Puncture," Circ Arrhythm Electrophysiol., 7(4):728-733 (2014).
Neven, K. et al., "Safety and Feasibility of Closed Chest Epicardial Catheter Ablation Using Electroporation," Circ Arrhythm Electrophysiol., 7:913-919 (2014).
Van Driel, V.J.H.M. et al., "Low vulnerability of the right phrenic nerve to electroporation ablation," Heart Rhythm, 12:1838-1844 (2015).
Van Driel, V.J.H.M. et al., "Pulmonary Vein Stenosis After Catheter Ablation Electroporation Versus Radiofrequency," Circ Arrhythm Electrophysiol., 7(4):734-738 (2014).
Wittkampf, F.H. et al., "Feasibility of Electroporation for the Creation of Pulmonary Vein Ostial Lesions," J Cardiovasc Electrophysiol, 22(3):302-309 (Mar. 2011).
Wittkampf, F.H. et al., "Myocardial Lesion Depth With Circular Electroporation Ablation," Circ. Arrhythm Electrophysiol., 5(3):581-586 (2012).
Notice of Reasons for Refusal received for Japanese Patent Application No. 2023-545295, mailed on May 21, 2024, 12 pages (6 pages of English Translation and 6 pages of Original Document).

\* cited by examiner

US 12,343,071 B2

VOLTAGE CONTROLLED PULSE SEQUENCES FOR IRREVERSIBLE ELECTROPORATION ABLATIONS

CROSS REFERENCE TO RELATED APPLICATION

This application claims priority to Provisional Application No. 63/142,133, filed Jan. 27, 2021, which is herein incorporated by reference in its entirety.

TECHNICAL FIELD

The present disclosure relates to medical apparatus, systems, and methods for ablating tissue in a patient. More specifically, the present disclosure relates to medical apparatus, systems, and methods for ablation of tissue by electroporation.

BACKGROUND

Ablation procedures are used to treat many different conditions in patients. Ablation may be used to treat cardiac arrhythmias, benign tumors, cancerous tumors, and to control bleeding during surgery. Usually, ablation is accomplished through thermal ablation techniques including radiofrequency (RF) ablation and cryoablation. In RF ablation, a probe is inserted into the patient and radio frequency waves are transmitted through the probe to the surrounding tissue. The radio frequency waves generate heat, which destroys surrounding tissue and cauterizes blood vessels. In cryoablation, a hollow needle or cryoprobe is inserted into the patient and cold, thermally conductive fluid is circulated through the probe to freeze and kill the surrounding tissue. RF ablation and cryoablation techniques indiscriminately kill tissue through cell necrosis, which may damage or kill otherwise healthy tissue, such as tissue in the esophagus, phrenic nerve cells, and tissue in the coronary arteries.

Another ablation technique uses electroporation. In electroporation, or electro-permeabilization, an electric field is applied to cells to increase the permeability of the cell membrane. The electroporation may be reversible or irreversible, depending on the strength of the electric field. If the electroporation is reversible, the increased permeability of the cell membrane may be used to introduce chemicals, drugs, and/or deoxyribonucleic acid (DNA) into the cell, prior to the cell healing and recovering. If the electroporation is irreversible, the affected cells are killed through apoptosis.

Irreversible electroporation (IRE) may be used as a non-thermal ablation technique. In IRE, trains of short, high voltage pulses are used to generate electric fields that are strong enough to kill cells through apoptosis. In ablation of cardiac tissue, IRE may be a safe and effective alternative to the indiscriminate killing of thermal ablation techniques, such as RF ablation and cryoablation. IRE may be used to kill targeted tissue, such as myocardium tissue, by using an electric field strength and duration that kills the targeted tissue but does not permanently damage other cells or tissue, such as non-targeted myocardium tissue, red blood cells, vascular smooth muscle tissue, endothelium tissue, and nerve cells.

SUMMARY

As recited in examples, Example 1 is an electroporation ablation system for treating targeted tissue in a patient. The electroporation ablation system comprises an ablation catheter including: catheter electrodes configured to generate electric fields in the targeted tissue in response to a plurality of electrical pulse sequences delivered in a plurality of therapy sections; a controller configured to: receive a first pulse voltage of a first electrical pulse sequence measured during a first therapy section of the plurality of therapy sections; determine a charge voltage based on the first pulse voltage; and an electroporation generator. The electroporation generator is operatively coupled to the catheter electrodes and the controller and configured to deliver a second electrical pulse sequence at a controlled pulse voltage for a second therapy section of the plurality of therapy sections, the second therapy section being after the first therapy section, the controlled pulse voltage being associated with the charge voltage.

Example 2 is the electroporation ablation system of Example 1, wherein the electroporation generator comprises a capacitor bank and the electroporation generator is configured to charge the capacitor bank to a voltage level of the charge voltage before a start of the second therapy section.

Example 3 is the electroporation ablation system of Example 1 or 2, wherein the first electrical pulse sequence comprises a plurality of first electrical pulses.

Example 4 is the electroporation ablation system of Example 3, wherein the first pulse voltage comprises one or more pulse voltages of the plurality of first electrical pulses measured during the first therapy section.

Example 5 is the electroporation ablation system of any one of Examples 1-4, wherein the controller is further configured to receive a first pulse current of the first electrical pulse sequence delivered during the first therapy section, wherein the controller is further configured to determine the charge voltage based on the first pulse voltage and the first pulse current.

Example 6 is the electroporation ablation system of Example 5, wherein the controller is further configured to determine a first tissue impedance based on the first pulse voltage and the first pulse current.

Example 7 is the electroporation ablation system of Example 6, wherein the controlled pulse voltage is a portion of the charge voltage.

Example 8 is the electroporation ablation system of Example 7, wherein a ratio of the controlled pulse voltage and the charge voltage is associated with the first tissue impedance.

Example 9 is the electroporation ablation system of any one of Examples 1-8, wherein the electroporation generator is further configured to deliver a scan electrical pulse sequence at a scan voltage during a scan section prior to the plurality of therapy sections, wherein the controller is further configured to determine an initial tissue impedance based on an initial pulse voltage of the scan electrical pulse sequence and an initial pulse current of the scan electrical pulse sequence measured during the scan section, wherein the controller is further configured to determine an initial charge voltage based on the initial tissue impedance.

Example 10 is the electroporation ablation system of Example 9, wherein the scan voltage is less than the controlled pulse voltage.

Example 11 is the electroporation ablation system of Example 9, wherein the scan electrical pulse sequence includes a single non-ablative electrical pulse.

Example 12 is method of using an electroporation ablation device. The method includes the steps of: disposing a catheter of the electroporation ablation device anatomically proximate to a target ablation location, the catheter comprising one or more catheter electrodes and configured to generate electric fields in response to a plurality of electrical pulse sequences delivered in a plurality of therapy sections; receiving a first pulse voltage of a first electrical pulse sequence measured during a first therapy section of the plurality of therapy sections; determining a charge voltage based on the first pulse voltage; and delivering a second electrical pulse sequence at a controlled pulse voltage for a second therapy section of the plurality of therapy sections, the second therapy section being after the first therapy section, the controlled pulse voltage being associated with the charge voltage.

Example 13 is the method of Example 12, further comprising: receiving a first pulse current of first electrical pulse sequence measured during the first therapy section, wherein determining a charge voltage comprises determining the charge voltage based on the first pulse voltage and the first pulse current.

Example 14 is the method of Example 13, further comprising: determining a first tissue impedance based on the first pulse voltage and the first pulse current, wherein determining a charge voltage comprises determining the charge voltage based on the first tissue impedance.

Example 15 is the method of any one of Examples 12-14, further comprising: delivering a scan electrical pulse sequence during a scan section; receiving an initial pulse voltage of the scan electrical pulse sequence measured during the scan section; receiving an initial pulse current of the scan electrical pulse sequence measured during the scan section; and determining an initial tissue impedance based on the initial pulse voltage and the initial pulse current measured, wherein the scan section is before the first therapy section, wherein the scan electrical pulse sequence is at a scan pulse voltage lower than the controlled pulse voltage.

Example 16 is an electroporation ablation system for treating targeted tissue in a patient. The electroporation ablation system comprising: an ablation catheter including: catheter electrodes configured to generate electric fields in the targeted tissue in response to a plurality of electrical pulse sequences delivered in a plurality of therapy sections; a controller configured to receive a first pulse voltage of a first electrical pulse sequence measured during a first therapy section of the plurality of therapy sections; determine a charge voltage based on the first pulse voltage; and an electroporation generator. The electroporation generator is operatively coupled to the catheter electrodes and the controller and configured to deliver a second electrical pulse sequence at a controlled pulse voltage for a second therapy section of the plurality of therapy sections, the second therapy section being after the first therapy section, the controlled pulse voltage being associated with the charge voltage.

Example 17 is the electroporation ablation system of Example 16, wherein the electroporation generator comprises a capacitor bank and the electroporation generator is configured to charge the capacitor bank to a voltage level of the charge voltage before a start of the second therapy section.

Example 18 is the electroporation ablation system of Example 16, wherein the first electrical pulse sequence comprises a plurality of first electrical pulses.

Example 19 is the electroporation ablation system of Example 18, wherein the first pulse voltage comprises one or more pulse voltages of the plurality of first electrical pulses measured during the first therapy section.

Example 20 is the electroporation ablation system of Example 16, wherein the controller is further configured to receive a first pulse current of a first electrical pulse sequence delivered during the first therapy section, wherein the controller is further configured to determine the charge voltage based on the first pulse voltage and the first pulse current.

Example 21 is the electroporation ablation system of Example 20, wherein the controller is further configured to determine a first tissue impedance based on the first pulse voltage and the first pulse current.

Example 22 is the electroporation ablation system of Example 21, wherein the controlled pulse voltage is a portion of the charge voltage.

Example 23 is the electroporation ablation system of Example 22, wherein a ratio of the controlled pulse voltage and the charge voltage is associated with the first tissue impedance.

Example 24 is the electroporation ablation system of Example 16, wherein the electroporation generator is further configured to deliver a scan electrical pulse sequence at a scan voltage during a scan section prior to the plurality of therapy sections, wherein the controller is further configured to determine an initial tissue impedance based on an initial pulse voltage of the scan electrical pulse sequence and an initial pulse current of the scan electrical pulse sequence measured during the scan section, wherein the controller is further configured to determine an initial charge voltage based on the initial tissue impedance.

Example 25 is the electroporation ablation system of Example 24, wherein the scan voltage is less than the controlled pulse voltage.

Example 26 is the electroporation ablation system of Example 24, wherein the scan electrical pulse sequence includes a single non-ablative electrical pulse.

Example 27 is the electroporation ablation system of Example 16, wherein the electroporation generator comprises a plurality of capacitor banks, wherein the electroporation generator is configured to charge at least one of the plurality of capacitor banks to a voltage level individually.

Example 28 is the electroporation ablation system of Example 27, wherein the electroporation generator is configured to use a first capacitor bank of the plurality of capacitor banks to deliver a pulse sequence for a specific therapy section of the plurality of therapy sections and charge a second capacitor bank of the plurality of capacitor banks to a voltage level of a determined charge voltage before a start of a therapy section immediately after the specific therapy section of the plurality of therapy sections.

Example 29 is the electroporation ablation system of Example 27, wherein the catheter electrodes comprise a plurality of electrode pairs, wherein each capacitor bank of the plurality of capacitor banks is operatively coupled to one or more electrode pairs of the plurality of electrode pairs.

Example 30 is the electroporation ablation system of Example 29, wherein the controller is configured to determine a bank charge voltage for each capacitor bank of the plurality of capacitor banks.

Example 31 is a method of using an electroporation ablation device. The method includes the step of: disposing a catheter of the electroporation ablation device anatomically proximate to a target ablation location, the catheter comprising one or more catheter electrodes and configured to generate electric fields in response to a plurality of electrical pulse sequences delivered in a plurality of therapy sections; receiving a first pulse voltage of a first electrical pulse sequence measured during a first therapy section of the plurality of therapy sections; determining a charge voltage based on the first pulse voltage; and delivering a second electrical pulse sequence at a controlled pulse voltage for a second therapy section of the plurality of therapy sections, the second therapy section being after the first therapy section, the controlled pulse voltage being associated with the charge voltage.

Example 32 is the method of Example 31, further comprising: receiving a first pulse current of first electrical pulse sequence measured during the first therapy section, wherein determining a charge voltage comprises determining the charge voltage based on the first pulse voltage and the first pulse current.

Example 33 is the method of Example 32, further comprising: determining a first tissue impedance based on the first pulse voltage and the first pulse current, wherein determining a charge voltage comprises determining the charge voltage based on the first tissue impedance.

Example 34 is the method of Example 30, further comprising: delivering a scan electrical pulse sequence during a scan section; receiving an initial pulse voltage of the scan electrical pulse sequence measured during the scan section; receiving an initial pulse current of the scan electrical pulse sequence measured during the scan section; and determining an initial tissue impedance based on the initial pulse voltage and the initial pulse current measured, wherein the scan section is before the first therapy section, wherein the scan electrical pulse sequence is at a scan pulse voltage lower than the controlled pulse voltage.

Example 35 is the method of Example 34, wherein the scan pulse voltage is at a non-ablative voltage level.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
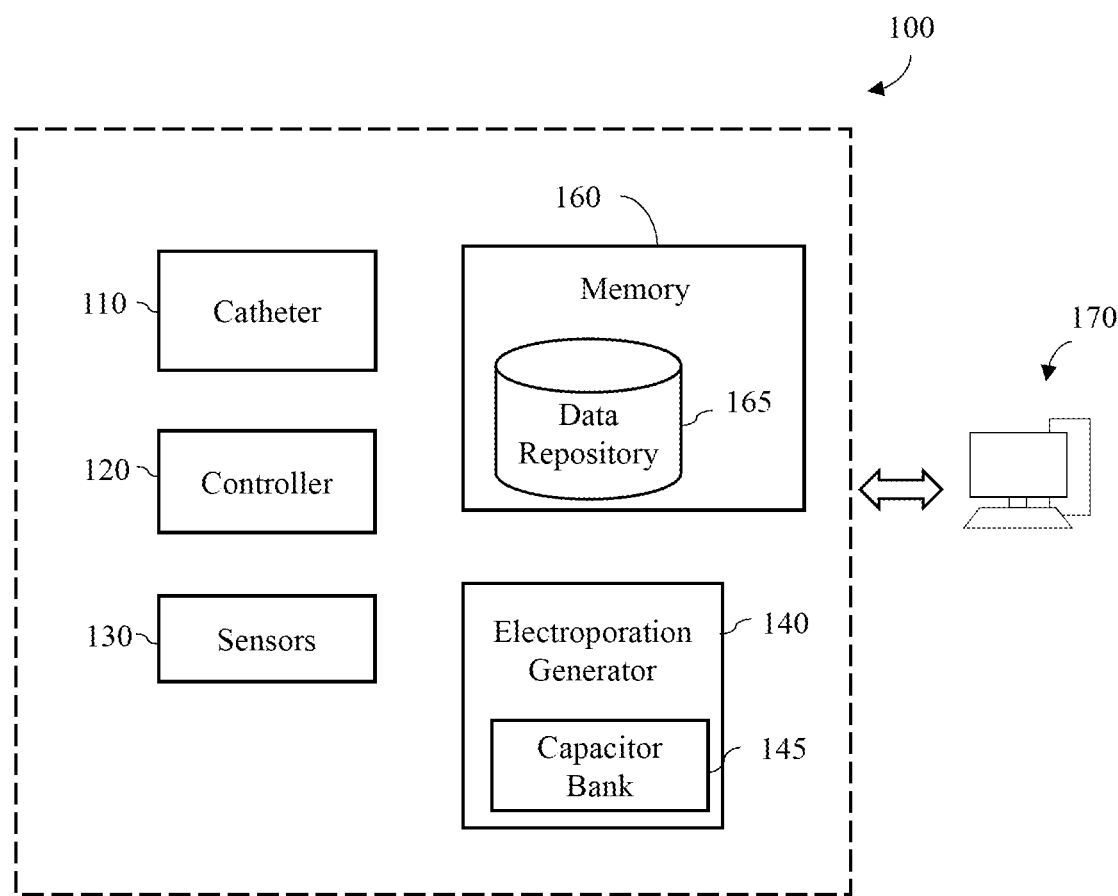
FIG. 1 depicts an illustrative system diagram for an electroporation ablation system, in accordance with embodiments of the subject matter of the disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

As the terms are used herein with respect to measurements (e.g., dimensions, characteristics, attributes, components, etc.), and ranges thereof, of tangible things (e.g., products, inventory, etc.) and/or intangible things (e.g., data, electronic representations of currency, accounts, information, portions of things (e.g., percentages, fractions), calculations, data models, dynamic system models, algorithms, parameters, etc.), "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error; differences in measurement and/or manufacturing equipment calibration; human error in reading and/or setting measurements; adjustments made to optimize performance and/or structural parameters in view of other measurements (e.g., measurements associated with other things); particular implementation scenarios; imprecise adjustment and/or manipulation of things, settings, and/or measurements by a person, a computing device, and/or a machine; system tolerances; control loops; machine-learning; foreseeable variations (e.g., statistically insignificant variations, chaotic variations, system and/or model instabilities, etc.); preferences; and/or the like.

Although illustrative methods may be represented by one or more drawings (e.g., flow diagrams, communication flows, etc.), the drawings should not be interpreted as implying any requirement of, or particular order among or between, various steps disclosed herein. However, certain some embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items, and, similarly, a subset or subgroup of items may include one or more items. A "plurality" means more than one.

As used herein, the term "based on" is not meant to be restrictive, but rather indicates that a determination, identification, prediction, calculation, and/or the like, is performed by using, at least, the term following "based on" as an input. For example, predicting an outcome based on a particular piece of information may additionally, or alternatively, base the same determination on another piece of information.

Cryo energy and radio-frequency (RF) energy kill tissues indiscriminately through cell necrosis, which can damage the esophagus, the phrenic nerve, coronary arteries, in addition to other undesired effects. Irreversible electroporation (IRE) uses high voltage, short (e.g., 100 microseconds or shorter) pulses to kill cells through apoptosis. IRE can be targeted to kill myocardium, sparing other adjacent tissues including the esophageal vascular smooth muscle and endothelium. After IRE ablation commences, pore induced in cell membranes and intracellular fluids are released into the extracellular matrix, such that tissue conductivity is increased and tissue impedance is decreased. Changes in tissue impedance occur rapidly, within the course of multiple IRE therapy sections, also referred to as therapy bursts or therapy sections. A therapy section (e.g., for a duration of 10 milliseconds) may include a plurality of electrical pulses (e.g., 20 pulses, 30 pulses, etc.) generated and delivered by an electroporation generator. If the electroporation generator does not adjust its charge voltage provided by source component(s), the therapeutic pulse voltage drops over the course of the IRE ablation by as much as 40%. Since the IRE treatment depends on the electric field, the drop of the pulse voltage can potentially impact the effectiveness of the IRE treatment.

The present disclosure describes systems, devices and methods for implementing ablation with voltage controlled electrical pulse sequences. In some embodiments, the pulse voltage and/or pulse current are measured during therapy sections and used to determine a charge voltage for the next therapy section, such that electrical pulses each has a voltage close to a target pulse voltage during the next therapy section. As used herein, the charge voltage refers to the voltage generated by the electroporation generator, which can be the voltage of one or more capacitor banks or other power source. In some embodiments, the tissue impedance is computed based on the pulse voltage and pulse current. In some cases, the tissue impedance is used to determine the charge voltage.

FIG. 1 depicts an illustrative system diagram for an electroporation ablation system 100, in accordance with embodiments of the subject matter of the disclosure. The electroporation ablation system 100 includes one or more electroporation ablation catheters 110, a controller 120, one or more sensors 130, an electroporation generator 140, and a memory 160. In embodiments, the electroporation ablation system 100 is configured to deliver electric field energy to target tissue in a patient's heart to create tissue apoptosis, rendering the tissue incapable of conducting electrical signals. In some cases, the electroporation ablation system 100 may connect with other system(s) 170, for example, a mapping system, an electrophysiology system, and/or the like.

In some embodiments, the catheter(s) 110 can be various types and forms of electroporation catheter such as, for example, linear ablation catheters, focal ablation catheters, circumferential catheters, and/or the like. In embodiments, the electroporation ablation system 100 includes an introducer sheath (not shown) operable to provide a delivery conduit through which the electroporation ablation catheter 110 can be deployed to specific target sites within a patient's cardiac chamber. In some cases, the electroporation ablation catheter 110 includes a shaft having a distal end and catheter electrodes situated at the distal end of the shaft and spatially arranged to generate electric fields in the targeted tissue in response to a plurality of electrical pulse sequences delivered in a plurality of therapy sections. In some cases, the catheter(s) 110 include deflectable catheter(s).

In some cases, the catheter(s) 110 includes one or more electrodes to generate an electric field for ablation. The electroporation generator 140, also referred to as a pulse generator, is configured to generate ablative pulse/energy, or referred to as electroporation pulse/energy, to be delivered to electrodes of the catheter(s) 110. The electroporation pulse is typically high voltage and short pulse. The controller 120 is configured to control functional aspects of the electroporation ablation system 100. In embodiments, the electroporation controller 120 is configured to control the electroporation generator 140 on the generation and delivery of ablative energy to electrodes of the catheter(s) 110 is individually addressable. In one case, each of the one or more electrodes of the catheter(s) 110. In such case, the controller 120 may control the ablative energy delivery to each electrode.

In some embodiments, the electroporation controller 120 can control an output voltage (i.e. the pulse voltage of pulse sequences) generated by the electroporation generator 140. In some embodiments, the electroporation generator 140 includes a capacitor bank 145, which can be charged and discharged for the generation of the charge voltage to generate electrical pulses. In some cases, the electroporation controller 120 can determine a charge voltage of the capacitor bank 145 in response to the sensing data. In some implementations, the charge voltage is the voltage generated by the electricity source component(s) (e.g., the capacitor bank 145) of the electroporation generator 140. In some cases, the capacitor bank 145 includes one or more capacitor banks such that at least one capacitor bank is to provide the charge voltage for the current therapy section (e.g., the current therapy burst) of the electrical pulses and at least one capacitor bank is to be charged for providing the charge voltage for the next therapy section (e.g., the next therapy burst) of electrical pulses. In some embodiments, the electroporation generator 140 has an internal impedance, or referred to as generator impedance. In some cases, the electroporation generator 140 can generate electrical pulses at a pulse voltage, or referred to as an output voltage, which is lower than the charge voltage because of the generator impedance. In some cases, the pulse voltage is a portion of the charge voltage. In some cases, a user can set up a target pulse voltage via an interface to the controller (e.g., a user interface, a software interface, a system interface).

In some embodiments, the electroporation controller 120 receives sensor data collected by sensor(s) of catheter(s) and/or sensors 130 placed proximate to the ablation location. In some cases, the controller 120 is configured to determine a tissue impedance based upon the measured pulse voltage and/or pulse current proximate to the electroporation location. In some cases, the controller 120 is configured to determine a charge voltage based on the measured pulse voltage and/or the tissue impedance. In some cases, the controller 120 is configured to determine a charge voltage based on the target pulse voltage, the generator impedance, and/or the tissue impedance. In some cases, the controller 120 is configured to control the capacitor bank 145 based on the determined charge voltage.

In some embodiments, the controller 120 is configured to receive a first pulse voltage and/or a first pulse current of a first electrical pulse sequence delivered during a first therapy section of a plurality of therapy sections. In some implementations, an electrical pulse sequence includes a plurality of the electrical/electroporation pulses for a therapy section. In some cases, the first pulse voltage and/or the first pulse current are measured for a last electrical pulse in a therapy section. In some cases, the first pulse voltage and/or the first pulse current are measured for a first electrical pulse in a therapy section. In some cases, the first pulse voltage and/or the first pulse current are determined based on measurements of a plurality of electrical pulses in a therapy section. In one example, the first pulse voltage and/or the first pulse current are an average voltage and/or current measured for a plurality of electrical pulses in a therapy section respectively. In one example, the first pulse voltage and/or the first pulse current are an average voltage and/or current measured for all the electrical pulses in the therapy section respectively.

In some embodiments, the controller 120 determines a charge voltage based on the first pulse voltage. In some cases, the controller 120 determines a charge voltage difference between the determined charge voltage and the current charge level of the capacitor bank 145. In some cases, the controller 120 determines a charge voltage difference based on a percentage difference between the measured pulse voltage and the target pulse voltage. For example, the charge voltage difference is determined by the current charge voltage multiplied by a percentage difference between the measured pulse voltage and the target pulse voltage. In some cases, the controller 120 controls or sets the capacitor bank 145 based on the determined charge voltage and/or the charge voltage difference. In some embodiments, the electroporation generator 140 is operatively coupled to the catheter electrodes and the controller 120 and configured to deliver a second electrical pulse sequence at a controlled pulse voltage for a second therapy section of the plurality of therapy sections, where the second therapy section is after the first therapy section. In some cases, the controlled pulse voltage is based at least in part on a determined charge voltage. In some cases, the capacitor bank 145 is set at the level of the determined charge voltage.

In some embodiments, the controller 120 is configured to determine the charge voltage for the second therapy section based on the first pulse voltage and the first pulse current. In some cases, the controller 120 is configured to determine a first tissue impedance based on the first pulse voltage and the first pulse current. In some cases, the controller 120 is configured to determine the charge voltage based on the first tissue impedance and the target pulse voltage. In some cases, the controller 120 is configured to determine the charge voltage based on the first tissue impedance, the target pulse voltage, and the generator impedance. In some embodiments, the electroporation generator 140 is configured to receive the signal indicative of the determined charge voltage and charge the capacitor bank 145 to the level of the determined charged voltage before the start of the next therapy section. In some cases, the controlled pulse voltage is a portion of the determined charge voltage. In some cases, the ratio of the controlled pulse voltage and the determined charge voltage is associated with the first tissue impedance.

Figure 2A:
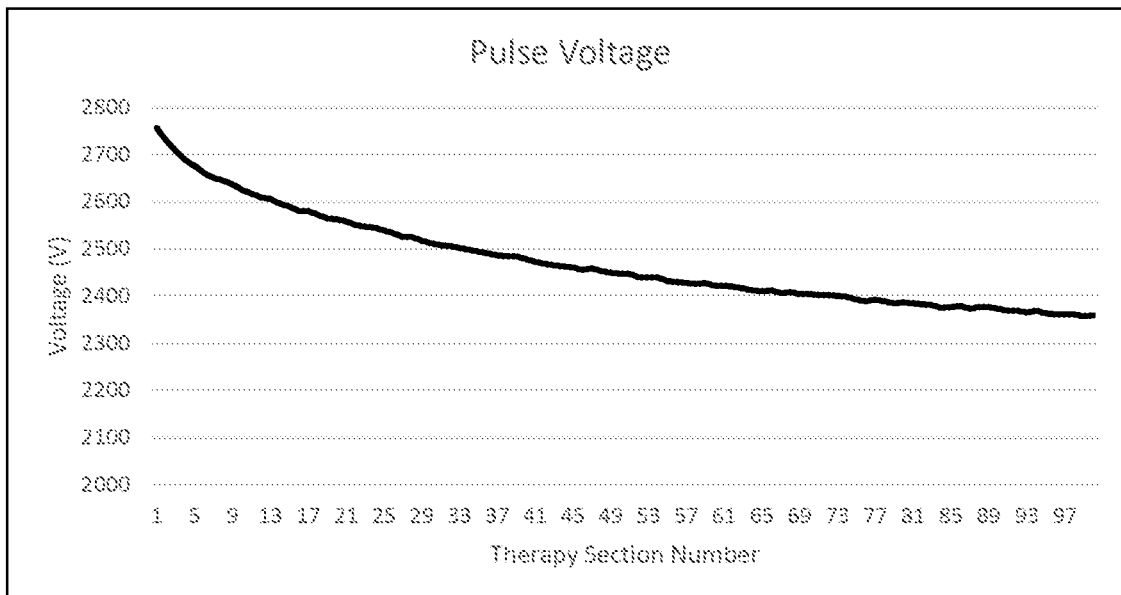
FIG. 2A is an illustrative graph of the pulse voltages changing over a number of therapy sections without adjusting the charge voltage.
Figure 2B:
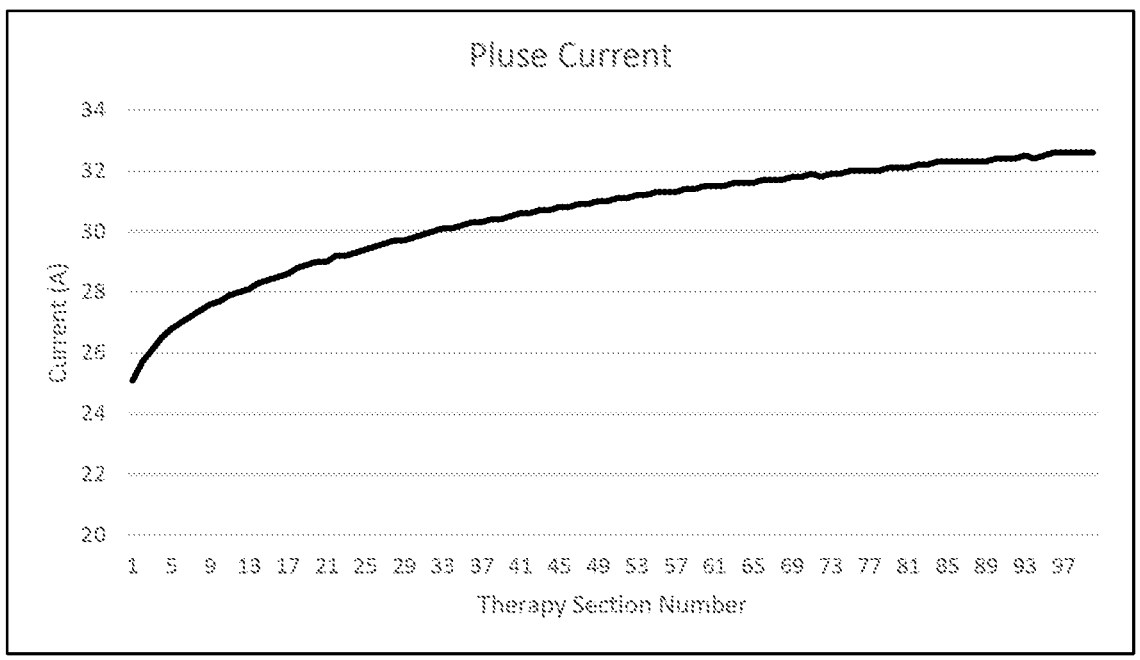
FIG. 2B is an illustrative graph of the pulse currents changing over a number of therapy sections without adjusting the charge voltage.
Figure 2C:
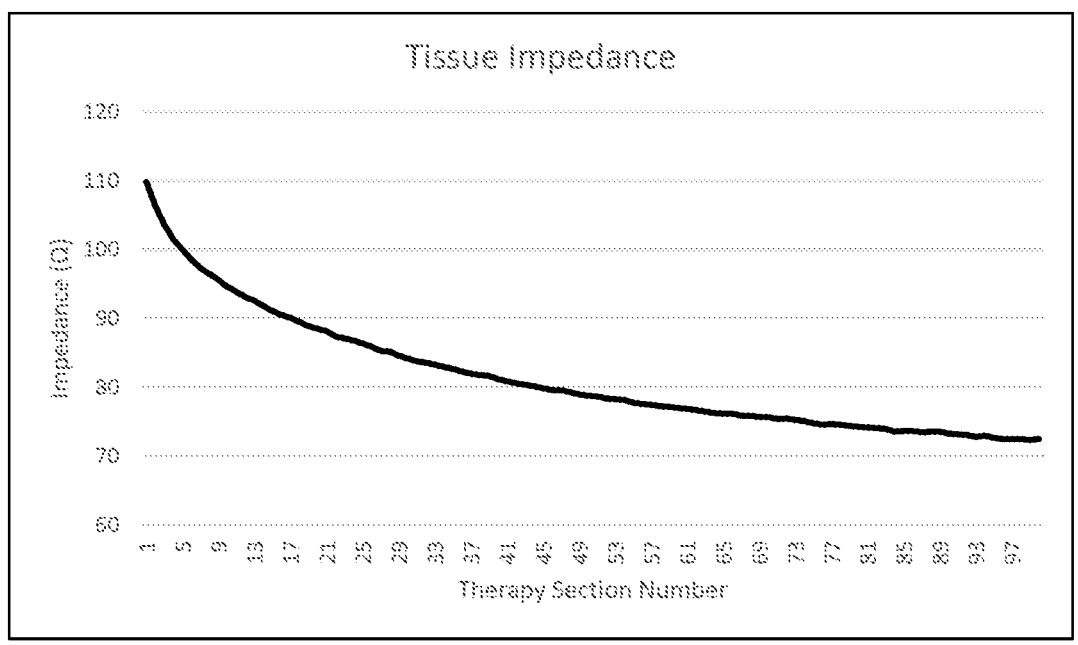
FIG. 2C is an illustrative graph of the tissue impedances changing over a number of therapy sections.

In embodiments, the controller 120 is configured to measure pulse voltages and/or pulse currents during each or some of the therapy sections to determine the charge voltages for the subsequent therapy sections. In some embodiments, the controller 120 is configured to store pulse voltages, pulse currents, charge voltages, generator impedance(s), and/or tissue impedances in the data repository 165. FIG. 2A is an illustrative graph of the pulse voltages changing over a number of therapy sections without adjusting the charge voltage. As shown, the pulse voltage decreases over the sequence of therapy sections. FIG. 2B is an illustrative graph of the pulse currents changing over a number of therapy sections without adjusting the charge voltage. As shown, the pulse current increases over the sequence of therapy sections. FIG. 2C is an illustrative graph of the tissue impedances changing over a number of therapy sections. As shown, the tissue impedance decreases over the sequence of therapy sections.

In some embodiments, the electroporation generator 140 is configured to deliver a scan electrical pulse sequence at a scan voltage during a scan section prior to the plurality of therapy sections, where the scan voltage is lower than the therapeutic voltage (e.g., the target pulse voltage). In some cases, the scan voltage is a non-ablative voltage level. In some cases, the scan electrical pulse sequence is a single non-ablative electrical pulse. In some cases, the controller 120 is configured to determine an initial tissue impedance based on an initial pulse voltage of the scan electrical pulse sequence and an initial pulse current of the scan electrical pulse sequence measured during the scan section. In some cases, the controller 120 is configured to determine an initial charge voltage based on the initial tissue impedance. In some cases, the controller 120 is configured to determine an initial charge voltage based on the initial tissue impedance and the target pulse voltage. In some cases, the controller 120 is configured to determine an initial charge voltage based on the initial tissue impedance, the target pulse voltage, and the generator impedance.

Figure 3:
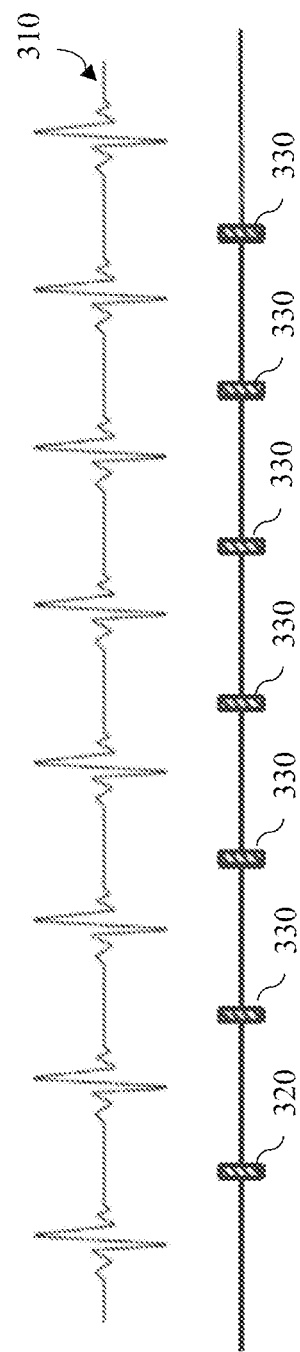
FIG. 3 is an illustrative example of a plurality of scan and therapy sections related to the cardiac beats.

FIG. 3 is an illustrative example of a plurality of scan and therapy sections related to the cardiac beats. As illustrated, the therapy sections 330 are provided between cardiac beats shown in the waveform 310. In this example, the scan section 320 is prior to the therapy sections 330. In some embodiments, the electroporation generator 140 is configured to charge the capacitor bank 145 to the determined charge voltage before the start of a respective therapy section. For example, with a cardiac beat rate of 90 BPM (beat-per-minute), the electroporation generator 140 is configured to charge the capacitor bank 145 to the level of the determined charge voltage within 667 milliseconds. In some cases, the electroporation controller 120 is configured to model the electric fields that can be generated by the catheter 110, which often includes consideration of the physical characteristics of the electroporation ablation catheter 110 including the electrodes and spatial relationships of the electrodes on the electroporation ablation catheter 110. In embodiments, the electroporation controller 120 is configured to control the electric field strength of the electric field formed by the electrodes of the catheter 110 to be no higher than 1500 volts per centimeter.

In some embodiments, the catheter 110 includes two or more electrode pairs of and the capacitor bank 145 includes two or more capacitor banks, where each capacitor bank in the capacitor bank 145 (e.g., a group of capacitor banks) is configured to charge one or more electrode pairs. In some cases, the electroporation controller 120 is configured to receive measured pulse voltages from the electrode pairs and determine a charge voltage for each respective capacitor bank for charging the electrode pairs. By way of an example, the capacitor bank 145 includes two capacitor banks (e.g., Bank A, Bank B), each capacitor bank is configured to charge two electrode pairs (e.g., Bank A for charging Electrode Pairs 1 & 2, Bank B for charging Electrode Pairs 3 & 4). In this example, the electroporation controller 120 is configured to determine a charge voltage for Bank A based on the measured pulse voltage of the Electrode Pairs 1 & 2, and determine a charge voltage for Bank B based on the measured pulse voltage of the Electrode Pairs 3 & 4.

In embodiments, the electroporation controller 120 includes one or more controllers, microprocessors, and/or computers that execute code out of memory 160, for example, non-transitory machine readable medium, to control and/or perform the functional aspects of the electroporation ablation system 100. In embodiments, the memory 160 can be part of the one or more controllers, microprocessors, and/or computers, and/or part of memory capacity accessible through a network, such as the world wide web. In embodiments, the memory 160 comprises a data repository 165, which is configured to store ablation data (e.g., location, energy, etc.), measured pulse voltages, measured pulse currents, tissue impedances, generator impedance, sensed data, treatment plan data, charge voltages, and/or the like.

In embodiments, the other systems 170 includes an electro-anatomical mapping (EAM) system. In some cases, the EAM system is operable to track the location of the various functional components of the electroporation ablation system 100, and to generate high-fidelity three-dimensional anatomical and electro-anatomical maps of the cardiac chambers of interest. In embodiments, the EAM system can be the RHYTHMIA™ HDx mapping system marketed by Boston Scientific Corporation. Also, in embodiments, the mapping and navigation controller of the EAM system includes one or more controllers, microprocessors, and/or computers that execute code out of memory to control and/or perform functional aspects of the EAM system.

The EAM system generates a localization field, via a field generator, to define a localization volume about the heart, and one or more location sensors or sensing elements on the tracked device(s), e.g., the electroporation ablation catheter 110, generate an output that can be processed by a mapping and navigation controller to track the location of the sensor, and consequently, the corresponding device, within the localization volume. In one embodiment, the device tracking is accomplished using magnetic tracking techniques, whereby the field generator is a magnetic field generator that generates a magnetic field defining the localization volume, and the location sensors on the tracked devices are magnetic field sensors.

In some embodiments, impedance tracking methodologies may be employed to track the locations of the various devices. In such embodiments, the localization field is an electric field generated, for example, by an external field generator arrangement, e.g., surface electrodes, by intrabody or intra-cardiac devices, e.g., an intracardiac catheter, or both. In these embodiments, the location sensing elements can constitute electrodes on the tracked devices that generate outputs received and processed by the mapping and navigation controller to track the location of the various location sensing electrodes within the localization volume.

In embodiments, the EAM system is equipped for both magnetic and impedance tracking capabilities. In such embodiments, impedance tracking accuracy can, in some instances be enhanced by first creating a map of the electric field induced by the electric field generator within the cardiac chamber of interest using a probe equipped with a magnetic location sensor, as is possible using the aforementioned RHYTHMIA HDx™ mapping system. One exemplary probe is the INTELLAMAP ORION™ mapping catheter marketed by Boston Scientific Corporation.

Regardless of the tracking methodology employed, the EAM system utilizes the location information for the various tracked devices, along with cardiac electrical activity acquired by, for example, the electroporation ablation catheter 110 or another catheter or probe equipped with sensing electrodes, to generate, and display via a display, detailed three-dimensional geometric anatomical maps or representations of the cardiac chambers as well as electro-anatomical maps in which cardiac electrical activity of interest is superimposed on the geometric anatomical maps. Furthermore, the EAM system can generate a graphical representation of the various tracked devices within the geometric anatomical map and/or the electro-anatomical map.

According to embodiments, various components (e.g., the controller 120) of the electroporation ablation system 100 may be implemented on one or more computing devices. A computing device may include any type of computing device suitable for implementing embodiments of the disclosure. Examples of computing devices include specialized computing devices or general-purpose computing devices such as workstations, servers, laptops, portable devices, desktop, tablet computers, hand-held devices, general-purpose graphics processing units (GPGPUs), and the like, all of which are contemplated within the scope of FIG. 1 with reference to various components of the system 100.

In some embodiments, a computing device includes a bus that, directly and/or indirectly, couples the following devices: a processor, a memory, an input/output (I/O) port, an I/O component, and a power supply. Any number of additional components, different components, and/or combinations of components may also be included in the computing device. The bus represents what may be one or more busses (such as, for example, an address bus, data bus, or combination thereof). Similarly, in some embodiments, the computing device may include a number of processors, a number of memory components, a number of I/O ports, a number of I/O components, and/or a number of power supplies. Additionally, any number of these components, or combinations thereof, may be distributed and/or duplicated across a number of computing devices.

In some embodiments, the memory 160 includes computer-readable media in the form of volatile and/or nonvolatile memory, transitory and/or non-transitory storage media and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In some embodiments, the memory 160 stores computer-executable instructions for causing a processor (e.g., the controller 120) to implement aspects of embodiments of system components discussed herein and/or to perform aspects of embodiments of methods and procedures discussed herein.

Computer-executable instructions may include, for example, computer code, machine-useable instructions, and the like such as, for example, program components capable of being executed by one or more processors associated with a computing device. Program components may be programmed using any number of different programming environments, including various languages, development kits, frameworks, and/or the like. Some or all of the functionality contemplated herein may also, or alternatively, be implemented in hardware and/or firmware.

The data repository 165 may be implemented using any one of the configurations described below. A data repository may include random access memories, flat files, XML files, and/or one or more database management systems (DBMS) executing on one or more database servers or a data center. A database management system may be a relational (RDBMS), hierarchical (HDBMS), multidimensional (MDBMS), object oriented (ODBMS or OODBMS) or object relational (ORDBMS) database management system, and the like. The data repository may be, for example, a single relational database. In some cases, the data repository may include a plurality of databases that can exchange and aggregate data by data integration process or software application. In an exemplary embodiment, at least part of the data repository 165 may be hosted in a cloud data center. In some cases, a data repository may be hosted on a single computer, a server, a storage device, a cloud server, or the like. In some other cases, a data repository may be hosted on a series of networked computers, servers, or devices. In some cases, a data repository may be hosted on tiers of data storage devices including local, regional, and central.

Various components of the system 100 can communicate via or be coupled to via a communication interface, for example, a wired or wireless interface. The communication interface includes, but not limited to, any wired or wireless short-range and long-range communication interfaces. The wired interface can use cables, umbilicals, and the like. The short-range communication interfaces may be, for example, local area network (LAN), interfaces conforming known communications standard, such as Bluetooth® standard, IEEE 802 standards (e.g., IEEE 802.11), a ZigBee® or similar specification, such as those based on the IEEE 802.15.4 standard, or other public or proprietary wireless protocol. The long-range communication interfaces may be, for example, wide area network (WAN), cellular network interfaces, satellite communication interfaces, etc. The communication interface may be either within a private computer network, such as intranet, or on a public computer network, such as the internet.

Figure 4:
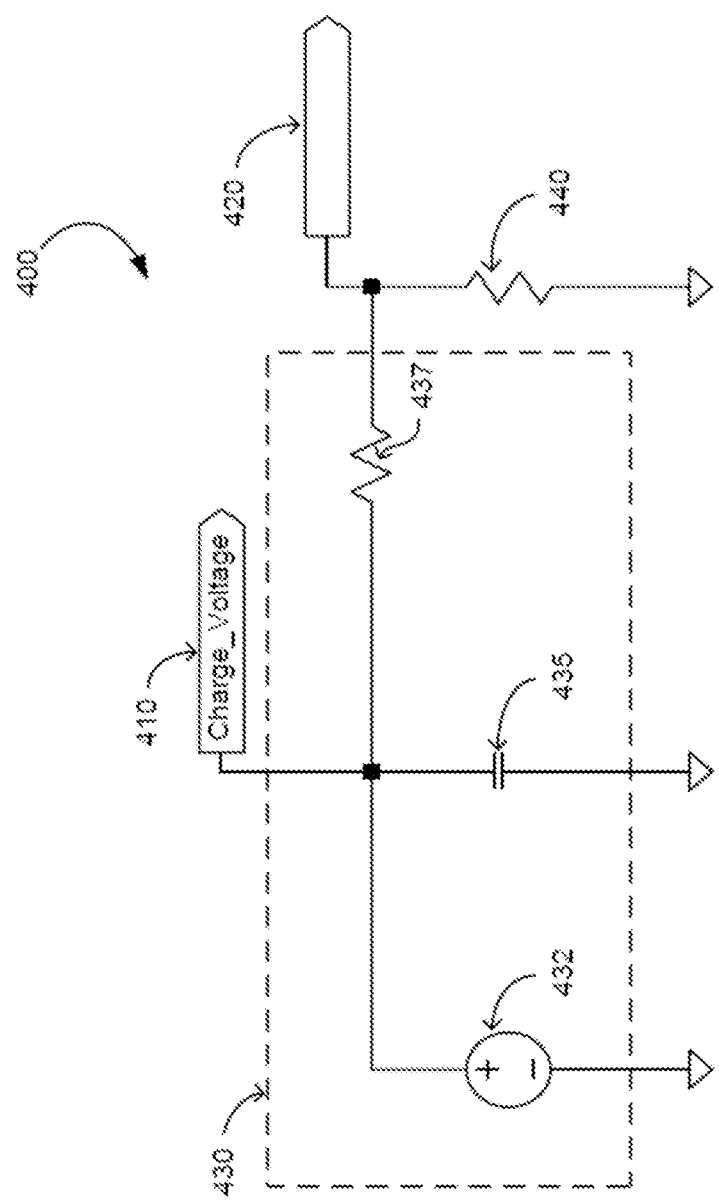
FIG. 4 is an illustrative schematic circuit diagram of an electroporation generator in use for an electroporation ablation section, in accordance with certain embodiments of the present disclosure.

FIG. 4 is an illustrative schematic circuit diagram 400 of an electroporation generator 430 in use for an electroporation ablation section, in accordance with certain embodiments of the present disclosure. In some implementations, other components can be included in the circuit diagram 400. In the circuit diagram 400, the electroporation generator 430 delivers electric pulse sequences at pulse_voltage 420 to target tissues. The target tissues have a tissue impedance 440, which is changing during the electroporation ablation section. In the simplified schematic diagram, the electroporation generator 430 includes a voltage source 432, a bulk capacitance 435 (e.g., a capacitor bank), and the generator impedance 437. In this example, the generator impedance 437 represents the overall impedance of the electroporation generator 430. In embodiments, the electroporation ablation section includes a plurality of therapy sections. In some embodiments, the voltage source 432 can charge the bulk capacitance 435 between therapy sections to adjust the charge_voltage 410 and thereby adjust the pulse_voltage 420 to reach the target pulse voltage.

In some embodiments, during a therapy section, a pulse_voltage or a plurality of pulse voltages are measured. In one example, the pulse_voltage 420 has a relation with the charge_voltage 410 represented in equation (1) below:

$$Voltage_{Pulse} = \frac{Voltage_{Charge} * Impedance_{Tissue}}{Impedance_{Generator} + Impedance_{Tissue}}, \quad (1)$$

where $Voltage_{Pulse}$ is the pulse_voltage 420, $Voltage_{charge}$ is the charge_voltage 410, $Impedance_{Tissue}$ represents the tissue impedance 440, and $Impedance_{Generator}$ is the generator impedance 437. Additionally, in one example, the charge_voltage 410 can be determined by the pulse_voltage 420 measured during the therapy sections, according the equation (2) below:

$$Voltage_{Charge} = \frac{Voltage_{Pulse} * Impedance_{Generator} + Impedance_{Tissue}}{Impedance_{Tissue}}, \quad (2)$$

where $Voltage_{Charge}$ is the voltage generated from the voltage source 432 and the bulk capacitance 435, $Voltage_{Pulse}$ is the pulse_voltage 420, $Impedance_{Tissue}$ represents the tissue impedance 440, and $Impedance_{Generator}$ is the generator impedance 437.

In some embodiments, a controller (e.g., the controller 120 of FIG. 1) is configured to determine and control the electroporation generator 430 using the equation (2) above. In some embodiments, a controller (e.g., the controller 120 of FIG. 1) is configured to determine and control the electroporation generator 430 using the other approaches to determine the charge_voltage. In some implementations, the electroporation generator 430 is configured to generate an electrical pulse sequence having a plurality of electrical/electroporation pulses (e.g., 2 microseconds electrical pulses with 500 microseconds between two adjacent pulses) during a therapy section (e.g., a therapy section of 10 milliseconds, a therapy section of 20 milliseconds etc.) during a cardiac beat.

Figure 5A:
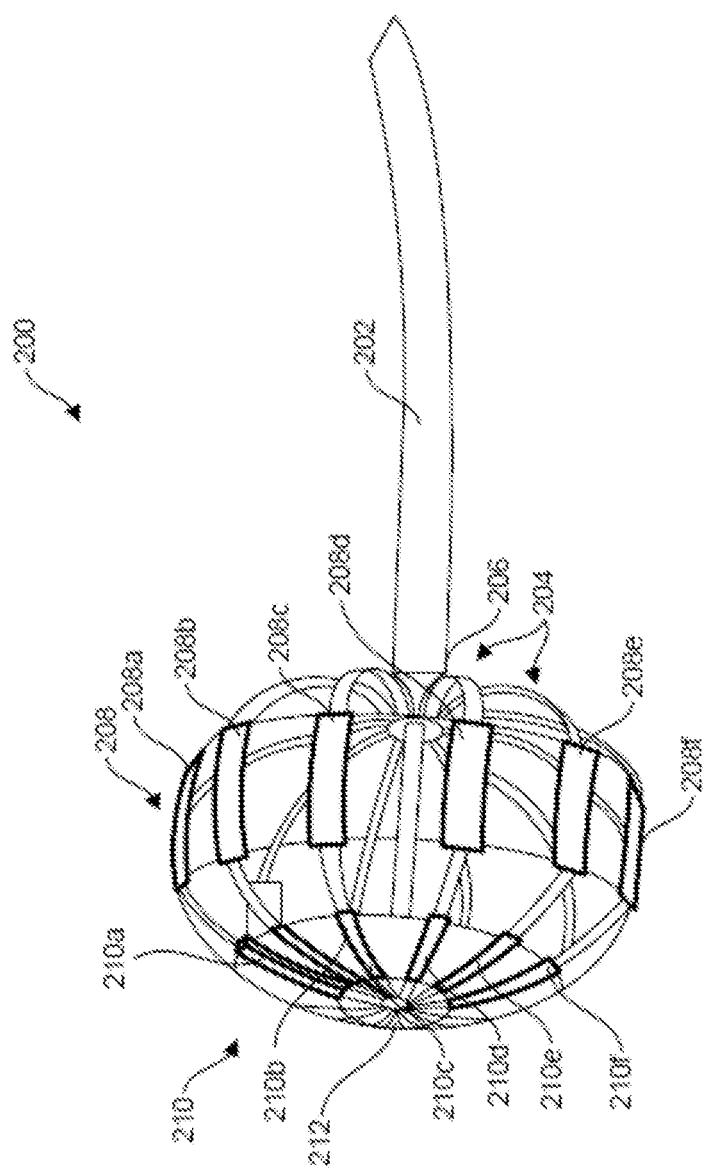
FIGS. 5A and 5B are diagrams illustrating example embodiments of catheters that can be used for electroporation, including ablation by irreversible electroporation, in accordance with embodiments of the subject matter of the disclosure.
Figure 5B:
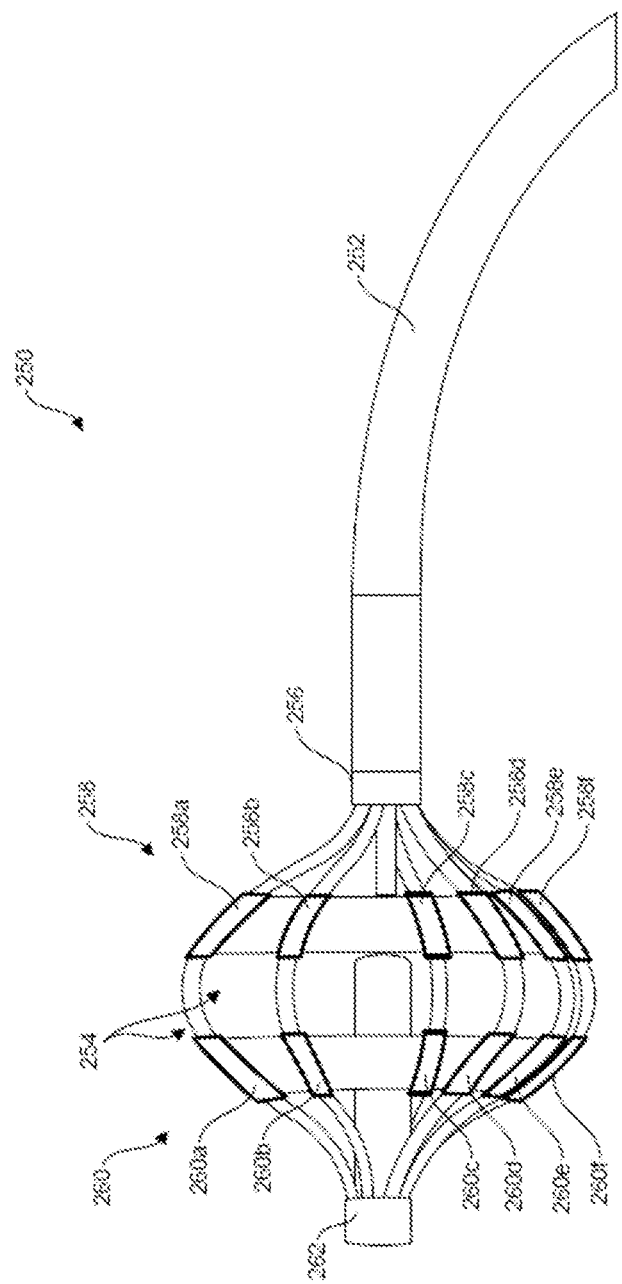

FIGS. 5A and 5B are diagrams illustrating example embodiments of catheters 200 and 250 that can be used for electroporation (e.g., catheter 110 in FIG. 1), including ablation by irreversible electroporation, in accordance with embodiments of the subject matter of the disclosure. The catheters 200 and 250 include electrodes, as described below, that are spaced apart from one another and configured to conduct electricity. Catheter characteristics are used to model electric fields that can be produced by the catheter. In embodiments, the characteristics used to model the electric fields can include: the type of catheter, such as a basket catheter that has a constant profile after being opened and a spline catheter that has a variable profile, which can be opened and closed by degree; the form factor of the catheter, such as a balloon catheter, a basket catheter, and a spline catheter; the number of electrodes; the inter-electrode spacing on the catheter; the spatial relationships and orientation of the electrodes, especially in relation to other electrodes on the same catheter; the type of material that the electrodes are made of; and the shape of the electrodes. In embodiments, the type of catheter and/or the form factor of the catheter includes catheters, such as linear ablation catheters and focal ablation catheters. In some cases, the type of catheter and/or the form factor of the catheter is not limited to those mentioned herein.

FIG. 5A is a diagram illustrating the catheter 200, in accordance with embodiments of the subject matter of the disclosure. The catheter 200 includes a catheter shaft 202 and a catheter basket 204 connected to the catheter shaft 202 at the distal end 206 of the catheter shaft 202. The catheter basket 204 includes a first group of electrodes 208 disposed at the circumference of the catheter basket 204 and a second group of electrodes 210 disposed adjacent the distal end 212 of the catheter basket 204. Each of the electrodes in the first group of electrodes 208 and each of the electrodes in the second group of electrodes 210 is configured to conduct electricity and to be operably connected to a controller (e.g., the controller 120 in FIG. 1) and an ablative energy generator (e.g., the electroporation generator 140 of FIG. 1). In embodiments, one or more of the electrodes in the first group of electrodes 208 and the second group of electrodes 210 includes metal.

Electrodes in the first group of electrodes 208 are spaced apart from electrodes in the second group of electrodes 210. The first group of electrodes 208 includes electrodes 208a-208f and the second group of electrodes 210 includes electrodes 210a-210f. Also, electrodes in the first group of electrodes 208, such as electrodes 208a-208f, are spaced apart from one another and electrodes in the second of electrodes 210, such as electrodes 210a-210f, are spaced apart from one another.

The spatial relationships and orientation of the electrodes in the first group of electrodes 208 and the spatial relationships and orientation of the electrodes in the second group of electrodes 210 in relation to other electrodes on the same catheter 200 is known or can be determined. In embodiments, the spatial relationships and orientation of the electrodes in the first group of electrodes 208 and the spatial relationships and orientation of the electrodes in the second group of electrodes 210 in relation to other electrodes on the same catheter 200 is constant, once the catheter is deployed.

As to electric fields, in embodiments, each of the electrodes in the first group of electrodes 208 and each of the electrodes in the second group of electrodes 210 can be selected to be an anode or a cathode, such that electric fields can be set up between any two or more of the electrodes in the first and second groups of electrodes 208 and 210. Also, in embodiments, each of the electrodes in the first group of electrodes 208 and each of the electrodes in the second group of electrodes 210 can be selected to be a biphasic pole, such that the electrodes switch or take turns between being an anode and a cathode. Also, in embodiments, groups of the electrodes in the first group of electrodes 208 and groups of the electrodes in the second group of electrodes 210 can be selected to be an anode or a cathode or a biphasic pole, such that electric fields can be set up between any two or more groups of the electrodes in the first and second groups of electrodes 208 and 210.

In embodiments, electrodes in the first group of electrodes 208 and the second group of electrodes 210 can be selected to be biphasic pole electrodes, such that during a pulse train including a biphasic pulse train, the selected electrodes switch or take turns between being an anode and a cathode, and the electrodes are not relegated to monophasic delivery where one is always an anode and another is always a cathode. In some cases, the electrodes in the first and second group of electrodes 208 and 210 can form electric fields with electrode(s) of another catheter. In such cases, the electrodes in the first and second group of electrodes 208 and 210 can be anodes of the fields, or cathodes of the fields.

Further, as described herein, the electrodes are selected to be one of an anode and a cathode, however, it is to be understood without stating it that throughout this disclosure the electrodes can be selected to be biphasic poles, such that they switch or take turns between being anodes and cathodes. In some cases, one or more of the electrodes in the first group of electrodes 208 are selected to be cathodes and one or more of the electrodes in the second group of electrodes 210 are selected to be anodes. Also, in embodiments, one or more of the electrodes in the first group of electrodes 208 can be selected as a cathode and another one or more of the electrodes in the first group of electrodes 208 can be selected as an anode. In embodiments, one or more of the electrodes in the second group of electrodes 210 can be selected as a cathode and another one or more of the electrodes in the second group of electrodes 210 can be selected as an anode.

FIG. 5B is a diagram illustrating the catheter 250, in accordance with embodiments of the subject matter of the disclosure. The catheter 250 includes a catheter shaft 252 and catheter splines 254 connected to the catheter shaft 252 at the distal end 256 of the catheter shaft 252. The catheter splines 254 includes a first group of electrodes 258 disposed proximal the maximum circumference of the catheter splines 254 and a second group of electrodes 260 disposed distal the maximum circumference of the catheter splines 254. Each of the electrodes in the first group of electrodes 258 and each of the electrodes in the second group of electrodes 260 is configured to conduct electricity and to be operably connected to the electroporation console (not shown). In embodiments, one or more of the electrodes in the first group of electrodes 258 and the second group of electrodes 260 includes metal.

Electrodes in the first group of electrodes 258 are spaced apart from electrodes in the second group of electrodes 260. The first group of electrodes 258 includes electrodes 258a-258f and the second group of electrodes 260 includes electrodes 260a-260f. Also, electrodes in the first group of electrodes 258, such as electrodes 258a-258f, are spaced apart from one another and electrodes in the second of electrodes 260, such as electrodes 260a-260f, are spaced apart from one another.

The spatial relationships and orientation of the electrodes in the first group of electrodes 258 and the spatial relationships and orientation of the electrodes in the second group of electrodes 260 in relation to other electrodes on the same catheter 250 are known or can be determined. In embodiments, the spatial relationships and orientation of the electrodes in the first group of electrodes 258 and the spatial relationships and orientation of the electrodes in the second group of electrodes 260 in relation to other electrodes on the same catheter 250 are variable, where the distal end 262 of the catheter 250 can be extended and retracted which changes the spatial relationships and orientation of the electrodes 258 and 260. In some embodiments, the spatial relationships and orientation of the electrodes in the first group of electrodes 258 and the spatial relationships and orientation of the electrodes in the second group of electrodes 260 on the same catheter 250 is constant, once the catheter 250 is deployed.

As to electric fields, in embodiments, each of the electrodes in the first group of electrodes 258 and each of the electrodes in the second group of electrodes 260 can be selected to be an anode or a cathode, such that electric fields can be set up between any two or more of the electrodes in the first and second groups of electrodes 258 and 260. Also, in embodiments, groups of the electrodes in the first group of electrodes 258 and groups of the electrodes in the second group of electrodes 260 can be selected to be an anode or a cathode, such that electric fields can be set up between any two or more groups of the electrodes in the first and second groups of electrodes 258 and 260. In some cases, the electrodes in the first and second group of electrodes 258 and 260 can form electric fields with electrode(s) of another catheter. In such cases, the electrodes in the first and second group of electrodes 258 and 260 can be anodes of the fields, or cathodes of the fields.

In some embodiments, one or more of the electrodes in the first group of electrodes 258 are selected to be cathodes and one or more of the electrodes in the second group of electrodes 260 are selected to be anodes. Also, in embodiments, one or more of the electrodes in the first group of electrodes 258 can be selected as a cathode and another one or more of the electrodes in the first group of electrodes 258 can be selected as an anode. In addition, in embodiments, one or more of the electrodes in the second group of electrodes 260 can be selected as a cathode and another one or more of the electrodes in the second group of electrodes 260 can be selected as an anode. Using the characteristics of the catheter 250 and the surrounding tissue, an electroporation controller (e.g., the controller 120 of FIG. 1) can determine models for the various electric fields that can be produced by the catheter 250.

Figure 6:
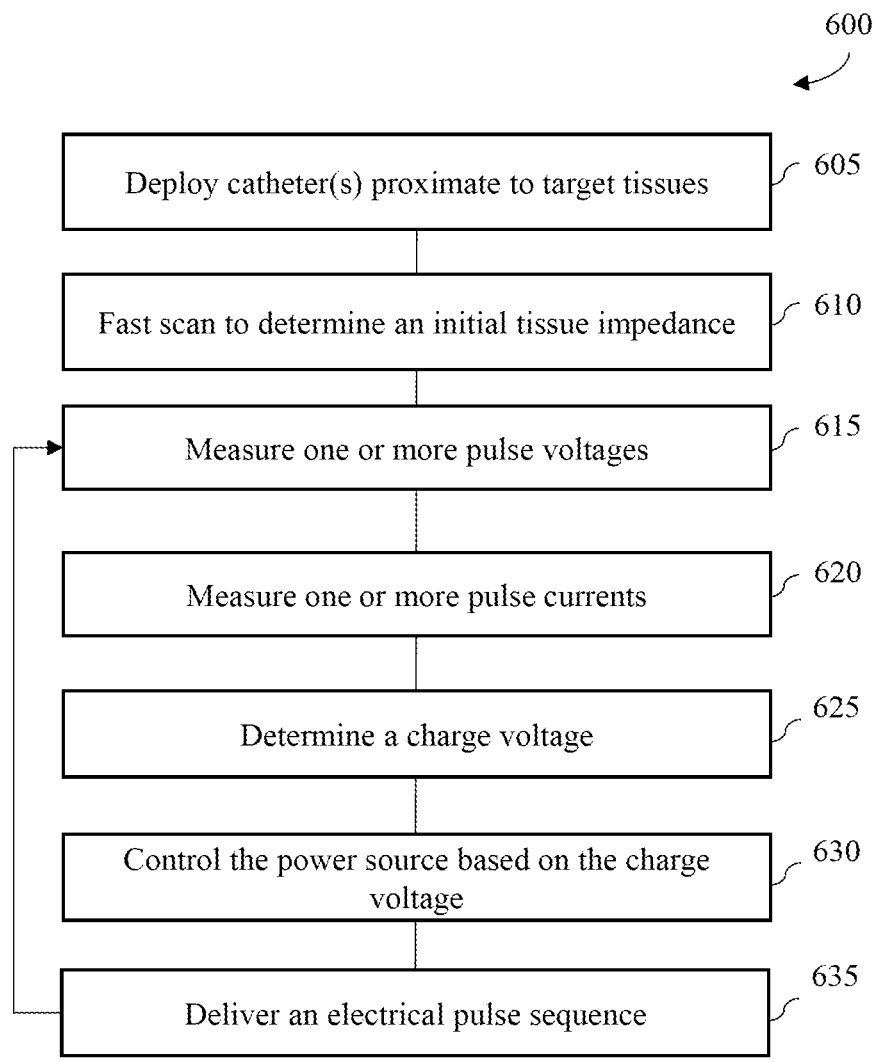
FIG. 6 is an example flow diagram depicting an illustrative method of using an electroporation ablation device, in accordance with some embodiments of the present disclosure.

FIG. 6 is an example flow diagram depicting an illustrative method 600 of using an electroporation ablation device, in accordance with some embodiments of the present disclosure. Aspects of embodiments of the method 600 may be performed, for example, by an electroporation ablation system (e.g., the system 100 depicted in FIG. 1). One or more steps of method 600 are optional and/or can be modified by one or more steps of other embodiments described herein. Additionally, one or more steps of other embodiments described herein may be added to the method 600. First, the electroporation ablation system deploys the electroporation ablation catheter(s) proximate to target tissues (605).

In some cases, the electroporation ablation system is configured to conduct a scan section to determine an initial tissue impedance (610). In some cases, the scan section is conducted before therapy sections. In some cases, the scan section includes a scan electrical pulse sequence at a scan voltage lower than the therapeutic pulse voltage. In one embodiment, the scan electrical pulse sequence includes a single non-ablative electrical pulse during the scan section. In some embodiments, the initial pulse voltage of the scan electrical pulse sequence and the initial pulse current of the scan electrical pulse sequence are measured during the scan section. In some cases, the initial pulse voltage and the initial pulse current are measured for a last electrical pulse in the scan electrical pulse sequence. In some cases, the initial pulse voltage and/or initial first pulse current is measured for a first electrical pulse of the scan electrical pulse sequence. In some cases, the initial pulse voltage and/or the initial pulse current are determined based on measurements of a plurality of electrical pulses in the scan electrical pulse sequence.

In one example, the initial pulse voltage and/or the initial pulse current are an average voltage and/or current measured for a plurality of electrical pulses in the scan section respectively. In one example, the initial pulse voltage and/or the initial pulse current are an average voltage and/or current measured for all the electrical pulses in the scan section respectively. In some embodiments, the initial tissue impedance is determined to be the initial pulse voltage divided by the initial pulse current. In some cases, the generator impedance can be determined by the charge voltage output from the capacitor bank (e.g., capacitor bank 145 of FIG. 1) and the measured pulse voltage, for example, using equation (1).

In some embodiments, the electroporation ablation system is configured to measure one or more pulse voltages (615), for example, during a therapy section. In some embodiments, the electroporation ablation system is configured to measure one or more pulse currents (620), for example, corresponding to the one or more pulse voltages. In some cases, a controller (e.g., the controller 120 in FIG. 1) of the electroporation ablation system is configured to determine a current tissue impedance using the one or more measured pulse voltages and/or the one or more measured pulse currents. In one implementation, the current tissue impedance is determined to be the pulse voltage divided by the pulse current. In one implementation, the current tissue impedance is determined to be the pulse voltage divided by the pulse current measured at the first electrical pulse during the therapy section.

In one implementation, the current tissue impedance is determined to be the pulse voltage divided by the pulse current measured at the last electrical pulse during the therapy section. In one implementation, the current tissue impedance is determined to be the pulse voltage divided by the pulse current. In one implementation, the current tissue impedance is determined based on a plurality of pulse voltages and a plurality of pulse currents measured during the therapy section. In some cases, the current tissue impedance is used to determine the charge voltage of the electroporation generator (i.e. the voltage generated by the electroporation generator). In some cases, the pulse voltage and/or pulse current are measured by sensors (e.g., sensors 130 in FIG. 1) deployed proximate to the target tissues. In some cases, the pulse voltage and/or pulse current are measured by sensors deployed with the catheter(s).

In some embodiments, the electroporation ablation system is configured to determine a charge voltage of the electroporation generator (e.g., electroporation generator 140 in FIG. 4) (625). In one example, the charge voltage is computed using equation (2). For example, if the measured pulse voltage of a prior therapy section is low by 100 volts from the target pulse voltage and assuming the generator impedance equal to the tissue impedance, the charge voltage is to be increased by 200 volts. In one implementation, the electroporation ablation system can set the capacitor bank (e.g., capacitor bank 145 in FIG. 4) with a 200-volt increase in the setting, such that the electrical pulse sequence is delivered at a voltage close to the target pulse voltage in the next therapy section.

In one embodiment, the electric field generated by electrodes of the deployed catheter(s) has a field strength no higher than 1500 volts per centimeter. In one embodiment, the electric field generated by electrodes of the deployed catheter(s) has a field strength higher than 500 volts per centimeter. In some embodiments, the electroporation ablation system is configured to control the power source based on the determined charge voltage (630), for example, by charging the capacitor bank based on the determined charge voltage. In some embodiments, the electroporation ablation system is configured to set the capacitor bank based on a voltage difference between the determined charge voltage and the current charge voltage of the power source.

In some embodiments, the electroporation ablation system is configured to deliver an electrical pulse sequence (635) for a next therapy section, for example, using the power source. In some cases, if the ablation therapy section has not ended, the electroporation ablation system goes back to step 615 to measure the one or more pulse voltages during the electrical pulse sequence (e.g., a plurality of electrical pulses delivered during a burst period) being delivered. In embodiments, the electroporation ablation system configured to measure pulse voltages and/or pulse currents during each or some of the therapy sections to determine the charge voltages for the subsequent therapy sections.

Various modifications and additions can be made to the exemplary embodiments discussed without departing from the scope of the present disclosure. For example, while the embodiments described above refer to particular features, the scope of the present disclosure also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An electroporation ablation system for treating targeted tissue in a patient, the electroporation ablation system comprising:
   an ablation catheter including:

catheter electrodes configured to generate electric fields in the targeted tissue in response to a plurality of electrical pulse sequences delivered in a plurality of therapy sections;

a controller configured to:
receive a first pulse voltage of a first electrical pulse sequence measured during a first therapy section of the plurality of therapy sections;
determine a charge voltage based on the first pulse voltage; and an electroporation generator operatively coupled to the catheter electrodes and the controller and configured to deliver a second electrical pulse sequence at a controlled pulse voltage for a second therapy section of the plurality of therapy sections, the second therapy section being after the first therapy section, the controlled pulse voltage being associated with the charge voltage wherein the electroporation generator is further configured to deliver a scan electrical pulse sequence at a scan voltage during a scan section prior to the plurality of therapy sections; and wherein the controller is further configured to determine an initial tissue impedance based on an initial pulse voltage of the scan electrical pulse sequence and an initial pulse current of the scan electrical pulse sequence measured during the scan section, and determine an initial charge voltage based on the initial tissue impedance.

2. The electroporation ablation system of claim 1, wherein the electroporation generator comprises a capacitor bank and the electroporation generator is configured to charge the capacitor bank to a voltage level of the charge voltage before a start of the second therapy section.

3. The electroporation ablation system of claim 1, wherein the first electrical pulse sequence comprises a plurality of first electrical pulses.

4. The electroporation ablation system of claim 3, wherein the first pulse voltage comprises one or more pulse voltages of the plurality of first electrical pulses measured during the first therapy section.

5. The electroporation ablation system of claim 1, wherein the controller is further configured to receive a first pulse current of a first electrical pulse sequence delivered during the first therapy section, wherein the controller is further configured to determine the charge voltage based on the first pulse voltage and the first pulse current.

6. The electroporation ablation system of claim 5, wherein the controller is further configured to determine a first tissue impedance based on the first pulse voltage and the first pulse current.

7. The electroporation ablation system of claim 6, wherein the controlled pulse voltage is a portion of the charge voltage.

8. The electroporation ablation system of claim 7, wherein a ratio of the controlled pulse voltage and the charge voltage is associated with the first tissue impedance.

9. The electroporation ablation system of claim 1, wherein the scan voltage is less than the controlled pulse voltage.

10. The electroporation ablation system of claim 1, wherein the scan electrical pulse sequence includes a single non-ablative electrical pulse.

11. The electroporation ablation system of claim 1, wherein the electroporation generator comprises a plurality of capacitor banks, wherein the electroporation generator is configured to charge at least one of the plurality of capacitor banks to a voltage level individually.

12. The electroporation ablation system of claim 11, wherein the electroporation generator is configured to use a first capacitor bank of the plurality of capacitor banks to deliver a pulse sequence for a specific therapy section of the plurality of therapy sections and charge a second capacitor bank of the plurality of capacitor banks to a voltage level of a determined charge voltage before a start of a therapy section immediately after the specific therapy section of the plurality of therapy sections.

13. The electroporation ablation system of claim 11, wherein the catheter electrodes comprise a plurality of electrode pairs, wherein each capacitor bank of the plurality of capacitor banks is operatively coupled to one or more electrode pairs of the plurality of electrode pairs.

14. The electroporation ablation system of claim 13, wherein the controller is configured to determine a bank charge voltage for each capacitor bank of the plurality of capacitor banks.

15. A method of using an electroporation ablation device, the method comprising:
disposing a catheter of the electroporation ablation device anatomically proximate to a target ablation location, the catheter comprising one or more catheter electrodes and configured to generate electric fields in response to a plurality of electrical pulse sequences delivered in a plurality of therapy sections;
receiving a first pulse voltage of a first electrical pulse sequence measured during a first therapy section of the plurality of therapy sections;
determining a charge voltage based on the first pulse voltage; and
delivering a second electrical pulse sequence at a controlled pulse voltage for a second therapy section of the plurality of therapy sections, the second therapy section being after the first therapy section, the controlled pulse voltage being associated with the charge voltage
delivering a scan electrical pulse sequence during a scan section;
receiving an initial pulse voltage of the scan electrical pulse sequence measured during the scan section;
receiving an initial pulse current of the scan electrical pulse sequence measured during the scan section; and
determining an initial tissue impedance based on the initial pulse voltage and the initial pulse current measured,
wherein the scan section is before the first therapy section,
wherein the scan electrical pulse sequence is at a scan pulse voltage lower than the controlled pulse voltage.

16. The method of claim 15, further comprising:
receiving a first pulse current of first electrical pulse sequence measured during the first therapy section,
wherein determining a charge voltage comprises determining the charge voltage based on the first pulse voltage and the first pulse current.

17. The method of claim 15, further comprising:
determining a first tissue impedance based on the first pulse voltage and the first pulse current,
wherein determining a charge voltage comprises determining the charge voltage based on the first tissue impedance.

18. The method of claim 15, wherein the scan pulse voltage is at a non-ablative voltage level.

* * * * *